(12) United States Patent
Dekany et al.

(10) Patent No.: US 6,953,850 B1
(45) Date of Patent: Oct. 11, 2005

(54) PROTECTING GROUPS FOR CARBOHYDRATE SYNTHESIS

(75) Inventors: Gyula Dekany, West Lake (AU); John Papagerogiou, Indooroopilly (AU); Laurent Francois Bornaghi, Forest Lake (AU)

(73) Assignee: Alchemia Pty. Ltd., Queensland (AU)

( * ) Notice: Subject to any disclaimer, the term of this patent is extended or adjusted under 35 U.S.C. 154(b) by 0 days.

(21) Appl. No.: 09/889,687

(22) PCT Filed: Jan. 18, 2000

(86) PCT No.: PCT/AU00/00025

§ 371 (c)(1),
(2), (4) Date: Jan. 25, 2000

(87) PCT Pub. No.: WO00/42057

PCT Pub. Date: Jul. 20, 2000

(30) Foreign Application Priority Data

Jan. 18, 1999 (AU) .............................................. PP8230

(51) Int. Cl.$^7$ ........................ C07H 15/20; C07H 15/22; C08F 212/08
(52) U.S. Cl. ........................ 536/124; 536/4.1; 536/18.5; 536/22.1; 536/25.3; 536/123.13; 525/333.6; 525/54.2; 560/29; 560/183; 562/508; 544/299; 568/327; 435/6; 436/518; 514/300
(58) Field of Search ........................ 536/124, 4.1, 18.5, 536/22.1, 25.3, 123.13, 23.13; 525/333.6, 54.2; 560/29, 183; 562/508; 544/299; 568/327; 435/6; 514/300; 436/518

(56) References Cited

U.S. PATENT DOCUMENTS 6,040,433 A * 3/2000 Kahne et al. ................. 536/4.1
6,538,117 B1 * 3/2003 Wong et al. ................ 536/18.5

FOREIGN PATENT DOCUMENTS

| EP | 0 578 112 | 1/1994 |
| EP | 578112 | * 1/1994 |
| WO | 95/08553 | 3/1995 |
| WO | 98/08799 | 3/1998 |
| WO | 98/38197 | 9/1998 |
| WO | 99/15510 | 4/1999 |

OTHER PUBLICATIONS

Chem. Abstracts, vol. 129, Abstract 203158; Angew. Chem., Int. Ed. (1998), 37(11), 1559–1561: RN 211947–41–0.
Chem Abstracts, vol. 127, Abstract 293496; J. Am. Chem. Soc. (1997), 119(42), 10064–10072: RN 196704–08–2.
Chem Abstracts, vol. 126, Abstract 75149; Angew. Chem. Int. Ed. Engl. (1996), 35 (21), 2510–2512: RN 185447–08–9.
Chem Abstracts, vol. 124, Abstract 109384, Bioconjugate Chem. (1996), 7(1), 45–55: RN 170966–45–7.

Chem Abstracts, vol. 122, Abstract 315043, JP 0625601 A2 (Rikagaku Kenkyusho, Japan; Otsuka Pharma Co Ltd) Sep. 13, 1994: RN 163214–35–5.
Chem Abstracts, vol. 121, Abstract 256150, J. Carbohydr. Chem. (1994), 13(2), 141–61: RN 158419–55–7.
Chem Abstracts, vol. 121, Abstract 157984, Chem. Lett. (1994), (6), 1049–52: RN 157428–35–5.
Chem Abstracts, vol. 119, Abstract 250313, Carbohydr. Res. (1993), 244(2), 259–73: RN 151072–08–1.
Chem Abstracts, vol. 116, Abstract 194721; Carbohydr. Res. (1992), 224, 111–22: RN 140420–79–7.
Chem Abstracts, vol. 112, Abstract 139667; J. Carbohydr. Chem. (1989), 8(4), 629–44: RN 125739–37–9.
Chem Abstracts, vol. 110, Abstract 39265; Carbohydr. Res. (1988), 179, 61–75: RN 118281–93–9.
Chem Abstracts, vol. 75, Abstract 36570; US 3574187 (Bannister) Apr. 6, 1971 [et.al.]: RN 34291–35–5.
Derwent Ab. AN 98–433880, JP 10182684 A (Toraday Ind Inc.) Jul. 7, 1998.

(Continued)

*Primary Examiner*—James O. Wilson
*Assistant Examiner*—Devesh Khare
(74) *Attorney, Agent, or Firm*—Haynes and Boone, LLP; Mark D. Moore

(57) ABSTRACT

The invention provides collections of orthogonally-protected monosaccharides as universal building blocks for the synthesis of glycoconjugates of non-carbohydrate molecules, neo-glycoconjugates and oligosaccharides. This orthogonal protection strategy allows for the specific deprotection of any substituent ono the saccharide ring, and greatly facilitates targeted or library-focused carbohydrate-related syntheses. In particular, the invention provides a universal monosaccharide building block of General Formula (I) or General Formula (II) in which A is a leaving group; X is hydrogen, O, N or $N_3$; $X_1$ is hydrogen, $—CH_2O—$, $—CH_2NH—$, $—CH_3$, $—CH_2N_3$ or $—COO—$; and B, C, D and E are protecting groups that can be cleaved orthogonally, and in which B, C, D and E are absent when X is hydrogen or $N_3$, and E is absent when $X_1$ is hydrogen, $CH_3$ or $N_3$.

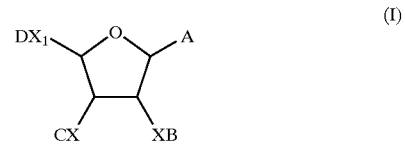

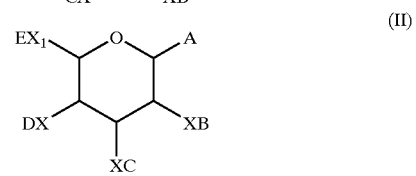

9 Claims, No Drawings

OTHER PUBLICATIONS

Chem Abstracts, vol. 131, Abstract 228893, Bioorg. Med. Chem. Lett. (1999), 9(14), 1911–1914: RN 244022–43–3.

Wong C–H et al., J. Am. Chem. Soc., 1998, 120, 7137–7138.

Wunderberg et al., Angew Chem. Int. Ed., 1998, 37, 2503–2505.

Supplementary Partial European Search Report from International Patent Application No. EP 00 90 2502, dated Sep. 27, 2002.

Tabeur et al., "L–iduronic acid derivatives as glycosyl donors," *Carbohydrate Research*, 281:253–76, 1996.

Ellervik et al., "Synthesis of lactam and acetamido analogues of sialyl Lewis X tetrasaccharide and Lewis X trisaccharide," *J. Organic Chem.*, 63:9323–38, 1998.

Sakairi et al., "Modification of cyclodextrins by insertion of heterogeneous sugar unit into their skeletons. Synthesis of 2–amino–2–epoxy–b–cyclodextrin from a–cyclodextrin," *J. Chem. Soc. Perkin Trans.*, 4:437–43, 1995.

Miayjima et al., "Lipid A and related compounds. XXXII. Synthesis of biologically active–N–acylated L–Homoserine–containing D–glucosamine–4–phosphate derivatives structurally related to lipid A," *Chem. Phar. Bull.*, 45:312–20, 1997.

Nicolaou et al., "A general and highly efficient solid phase synthesis of oligosaccharides. Total synthesis of a heptasaccharie phytoalexin elicitor (HPE)," *J. Am. Chem. Soc.*, 199:449–50, 1997.

Kloosterman et al., "Reductive introduction and oxidative removal of 4–methoxybenzyl ether in the presence of the azido group. Synthesis of a 2–azido–2–deoxy sugars having chain extension at C–4," *Recl. Trav. Chim. Pays–Bas*, 104:291–95, 1985.

Baeschlin et al., "Rapid assembly of oligosaccharides: Total synthesis of a glycosylphosphatidylinositol anchor of Trypanosoma brucei," *Agnew Chem. Int. Ed.*, 37:3423–28, 1998.

Ernst et al., "Oligosaccharide–analogues of polysaccharides. Part 8. Orthogonally protected cellobiose–derivated dialkynes. A convenience method for regioselective bromo–and protogermylation o trimethylgermyl–and trimethylsilyl–protected dialkynes," *Helvetica Chimica Acta*, 79:1279–94, 1996.

* cited by examiner

PROTECTING GROUPS FOR CARBOHYDRATE SYNTHESIS

This invention relates to methods of synthesis of glycoconjugates, and in particular to orthogonally protected carbohydrate building blocks. The invention provides collections of orthogonally protected monosaccharides as universal building blocks for the synthesis of glycoconjugates of non-carbohydrate molecules, neo-glycoconjugates and oligosaccharides. This orthogonal protection strategy allows for the specific deprotection of any substituent on the saccharide ring, and greatly facilitates targeted or library-focused carbohydrate related syntheses.

BACKGROUND OF THE INVENTION

Oligosaccahrides are important components of a variety of different types of biological molecules, and are involved in antigenic recognition and cell—cell interactions. In many cases, bio-molecules require conjugation with a carbohydrate component in order to be fully functional. In order to enable investigation of the biological function, and to exploit the exquisite biochemical and antigenic specificity of oligosaccharides, it is essential to have access to highly defined, specific synthetic oligosaccharides. Therefore achieving efficient, cost-effective synthesis of oligosaccharides and glycoconjugates by either solution or solid phase methods is of the utmost importance.

This task is enormously complicated by the complexity of oligosaccharides. Because of the number of sites which can carry substituents, and the number of possible ways in which two saccharide molecules can be linked, the number of permutations is enormously high.

In naturally-occurring oligosaccharides D-glucose, D-galactose L-fucose, D-mannose, D-glucosamine and D-galactosamine are among the most common sugar residues. To construct oligosaccharides and carbohydrates conjugates using these sugars, current methodologies require long, protracted syntheses, involving synthesis of as many as one hundred different specially-protected sugar donors in order to cover adequately all the possible permutations of glycosidic link formation (eg. 1-3, 1-4), link type (eg. $\alpha$ or $\beta$) and to include all possible branching points in the oligosaccharide.

Orthogonal protection of bi-functional molecules has been a widely used technique in organic chemistry, which provided general building blocks for selected syntheses. However, orthogonal protection in the case of molecules with a greater degree of functionalisation is quite rare. Our technology involves penta-functional monosaccharide building blocks, which require a much higher level of chemical specificity to attain the appropriate orthogonality.

Orthogonal protection has been defined by Merrifield as follows:

"The principle of orthogonal stability requires that only those protecting functions should be used that can be cleaved under different reaction conditions without affecting the other functions present" (Merrifield, 1977)

Orthogonal protecting strategies and conditions are reviewed in the textbook, "Protecting Groups in Organic Synthesis", by Green and Wicks (3rd edition). Although the use of orthogonal protection would greatly facilitate carbohydrate related synthesis, there has been limited success in devising suitable protecting groups and methods.

Wong et al. synthesised a universal building block with chloroacetyl, p-methoxybenzyl, levulinyl and tert-butyldiphenylsilyl protecting groups, selectively removably with sodium bicarbonate, trifluoroacetic acid, hydrazine and hydrogen fluoride-pyridine respectively, on a galactopyranose ring with an aryl-thio leaving group at the glycosidic position. This building block was used solely to syntheses a 6-hexanate glycoside. The subsequent recombinant oligosaccharide library formation focused on using the 6-hexane derivatised building block which exhibits only four degrees of orthogonality (Wong et al, 1998).

Similarly Kunz and coworkers synthesized an orthogonally protected D-glucopyranose derivative, but synthetic manipulations were only performed on the aglycon. These authors describe orthogonal protection of hydroxyl groups on a monosaccharide linked at C1 via a thioglycoside group to a solid support or to a succinimide moiety. In this case the protecting groups are acetyl or methy at C2, ally at C3, ethoxyethyl at C4, the tert-butyldiphenylsilyl at C6. The thioglycoside anchor functionalized in the side-chain is stated to be crucial. Again there is no suggestion that this protection system can be used for substituted sugars. Kunz's orthogonally-protected building block was not used for clycosylation or construction of glycoconjugates or neo-glycoconjugates, by directly attaching functionalities to the pyranose ring (Wunberg et al. 1998).

In our earlier International Patent Applications No. PCT/AU97/00544, No. PCT/AU98/00131 and No. PCT/AU98/00808, we described protecting and linking groups which enabled oligosaccharides and aminooligosaccharides to be synthesised using solid phase methods of the type which for many years have been used in peptide synthesis. In addition the protecting groups, described therein were useful for solution-phase synthesis. The entire disclosures of these specifications are incorporated herein by this reference.

We have now devised new types of building blocks which greatly facilitate the synthesis of oligosaccharides and glycoconjugates, using orthogonally-protected saccharide building blocks with five degrees of orthogonally. These building blocks contain a leaving group or latent leaving group at the glycosidic position, and another four orthogonally-protected functional groups around the carbohydrate ring.

Using our approach with six universal building blocks based on six of the most common naturally occurring sugars, any one of the one hundred sugars referred to above may be quickly synthesized in a facile manner, using simple, well-known protecting group chemistry. The years of work and complex protection strategies required to produce these one hundred building blocks by previously-available methods can be avoided by use of our six universal building blocks, which do not require a high level of skill to use, and enable one to achieve the synthesis of a specific desired oligosaccharide or glycoconjugate much faster and most efficiently than previously possible.

SUMMARY OF THE INVENTION

In its most general aspect the invention provides a universal monosaccharide building block of General Formula I or General Formula II

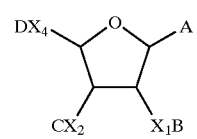

I

-continued

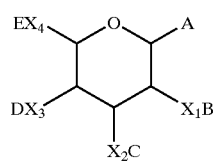

II in which

A is a leaving group, including but not limited to groups such as —SR, where R is alkyl, substituted alkyl, alkenyl, substituted alkenyl, alkynyl, substituted alkynyl, cycloalkyl, substituted cycloalkyl, aryl, substituted aryl, halogen; trichloroacetimidoyl-; sulphoxide; -O-alkenyl;

$X_1$, $X_2$, $X_3$ are independently selected from H, O, N, or $N_3$, with the provisio that only one of $X_1$, $X_2$, and $X_3$ may be H, N, or $N_3$ in any molecule;

$X_4$ is H, —$CH_2O$, —$CH_2N$, —$CH_3$, —$CH_2N_3$ or —COO—, with the proviso that $X_4$ may only be H, —$CH_2$, —$CH_3$ or —$CH_2N_3$ when none of $X_1$ to $X_3$ is H; and The following non-limiting sets have been designated as orthogonal to each other on the basis of their cleavage conditions. A protecting group is classified in a particular set according to its liability to the cleavage conditions for a particular set and its stability to the cleavage conditions required for the removal of those groups in the remaining sets. Each set is to be taken to include, but is not be limited, by the members thereof.

Of the sets defined, set 1, the 'Base Solvolysis' set, is of particular importance, because in addition to the fact that the members of this set are considered to be orthogonal to the members of the remaining sets, some members of this set are also considered to be orthogonal to each other. Where this is the case, the alternative condition of cleavage that provides orthogonality is specified in brackets following the listing of the protecting group.

1. Base Solvolysis
   a) for hydroxy protection:
      acyl-type protecting groups, eg. chloroacetate (also thiourea-sensitive)
      bromoacetate (also pyridine-sensitive)
      (carbonates, eg. Alloc ($Pd^0$))
      Fmoc (β-elimination)
      Troc
      p-nitrophenylsulphonylethyloxy carbonyl)
      levanoyl (also hydrazine sensitive)
   b) for amino protection:
      Dde, Wow (primary amine-sensitive)
      tetraphthaloyl
      dichlorophthaloyl
      2,5-dimethyl-pyrrol (primary amine-sensitive)
      benzyloxycarbonyl
      pentenyl
2. Fluoride Ion-Sensitive
   for hydroxy protection:
      t-butyldiphenylsilyl
      triisopropylsilyl
      trimethylsilylethyl
      triphenylsilylethyl
      (all cleavable with HF/Pyridine)
3. Reduction-Sensitive
   trifluoromethyl
   trichloromethyloxymethyl
   trichloromethyloxycarbonate
   (all cleavable with zinc/acetic acid)
4. β-Elimination-Sensitive, Base-Labile Protecting Groups
   ethoxyethyl
   cyanoethyl
   NSC (p-nitrogen-sulphonylethyloxycarbonyl)
   p-nitrobenzyl-sulphonylethyl
5. Hydrogenolysis-Sensitive Protecting Group
   naphthylmethyl
   substituted naphthylmethyl
6. Oxidation-Sensitive Protecting Groups:
   p-methyoxybenzyl
   3,4-dimethoxybenzyl
   2,4,6-trimethoxybenzyl
   3,4-methylenedioxybenzyl
   acylamidobenzyl
   azidobenzyl
   p-azido-m-chlorobenzyl
7. Allylic Protecting Groups
   Cleavable with $Pd^0$ complexes
8. Photolabile Protecting Groups:
   o-nitrobenzyloxycarbonate
   o-nitrobenzyl
   dinitrobenzyl
   2-oxo-1,2-diphenylethyl
9. Protecting Groups Removable by Relay Deprotection
   methylthioethyl
   acyloxybenzyl
   benzylthioethyl.

In one preferred embodiment, the invention provides a compound of General Formula III

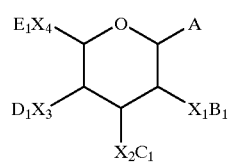

III in which

A, $X_1$, $X_2$, $X_3$ and $X_4$ are as defined for General Formulae I and II, and $B_1$, $C_1$, $D_1$ and $E_1$ are orthogonal carbohydrate protecting groups (ie. an orthogonal set) selected from protecting group sets 1, 2, 6 and 8.

Another preferred embodiment provides a compound of General Formula IV

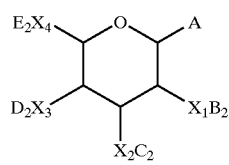

IV in which

A, $X_1$, $X_2$, $X_3$ and $X_4$ are as defined for General Formulae I and II, and $B_2$, $C_2$, $D_2$ and $E_2$ are selected from the members of protecting group set 1, and in themselves constitute and orthogonal set, for example the carbohydrate-protecting groups levanoyl (ammonia-labile), chloroacetate (thiourea-labile), p-methoxybenzyloxycarbonyl (oxidation-labile) and 2-trimethylsilylethylcarbonate (fluoride ion-labile).

This embodiment provides universal building blocks with protecting groups selected from the protecting groups of set 1.

In a third preferred embodiment the invention provides a compound of General Formula V

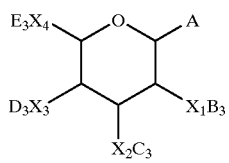

V in which

A, $X_1$, $X_2$, $X_3$ and $X_4$ are as defined for General Formula I and II, and $B_3$, $C_3$, $D_3$ and $E_3$ are an orthogonal set of protecting groups selected from amongst the members of set 1 and from the remaining orthogonal sets.

This embodiment provides orthogonally protected building blocks, the protecting group constituents of which may be selected from within set 1 and from the remaining sets.

It will be clearly understood that the invention is not limited to use with monosaccharides, but is also applicable to any compound in which substituents are linked to a pyranose or furanose ring, such as sugar analogues.

For the purposes of this specification it will be clearly understood that the word "comprising" means "including but not limited to", and that the word "comprises" has a corresponding meaning.

For the purposes of this specification "orthogonal cleavage" is defined as the regioselective cleavage of a hydroxy or amino protecting group from a carbohydrate, in which the cleavage conditions do not compromise the stability of the other protecting or functional groups on the molecule. Such cleavages can be effected in any order of priority. "Cleaved orthogonally" and "orthogonal cleavage" are taken to a synonymous.

DETAILED DESCRIPTION OF THE INVENTION

Abbreviations used herein are as follows:

| Alloc | Allyloxycarbonyl |
|---|---|
| Bn | Benzyl |
| Bu | Butyl |
| DCM | Dichloromethane |
| Dde | N-1-(4,4-Dimethyl-2,6-dioxocyclohexylidene)ethyl |
| Dde-OH | 6-Hydroxy-6-(4,4-dimethyl-2,6-dioxocyclohexylidene)ethyl |
| DMAP | N,N'-Dimethylaminopyridine |
| DMF | N,N'-Dimethylformamide |
| DMTST | Dimethyl(methylthio)sulphoniumtrifluoromethanesulphonate |
| EEDQ | 1-isobutyloxycarbonyl-2-isobutyloxy-1,2-dihydroquinoline |
| EtOAc | Ethyl acetate |
| EtOH | Ethanol |
| FAB-MS | Fast atom bombardment mass spectrometry |
| HRMS | High resolution mass spectrometry |
| Fmoc | Fluoromethoxycarbonyl |
| MBHA | Methyl benzyhydryamine resin |
| Me | Methyl |
| MeOH | Methanol |
| NCS | p-Nitrobenzyl-sulphonylethyloxycarbonyl |
| NMR | Nuclear magnetic resonance |
| ODmab | 4-{N-[1-(4,4-dimethyl-2,6-dioxocyclohexylidene)-3-methylbutyl]-amino}benzyl alcohol |
| PEG | Polyethylene glycol |
| tBu | Tertiary-butyl |
| TFA | Trifluoroacetic acid |
| THF | Tetrahydrofuran |
| Troc | 2,2,2-Trichloroethoxycarbonyl |

The invention provides universal building blocks, which are useful in the solution and solid phase synthesis of oligosaccharides. The reaction scheme for synthesis of each target molecule is designed so as to specify the orthogonally-protected functional groups which may be freed for glycosylation, and those which need to be capped with a protecting group such as benzyl, benzoyl, or another such group which remains uncleaved until the end of the synthesis, in order to avoid competition during glycosylations later in the synthesis.

When participation during the glycosylation reaction is required, the 2-hydroxyl is selectively deprotected and re-protected with a benzoyl group which, again, remains until the completion of the synthesis. In the case of 2-deoxy 2-aminosugars, if participation or stereoselectivity is required the Dde group might be removed and replaced with a tetrachlorophthaloyl or 2,5-dimethylpyrrole group.

EXAMPLE 1

Synthesis of an Exemplary Tetrasaccharide

A strategy for synthesis of the tetrasaccharide of formula VI is set out in Scheme 1.

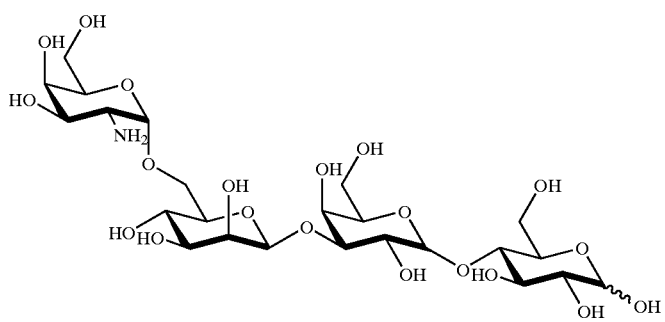

VI

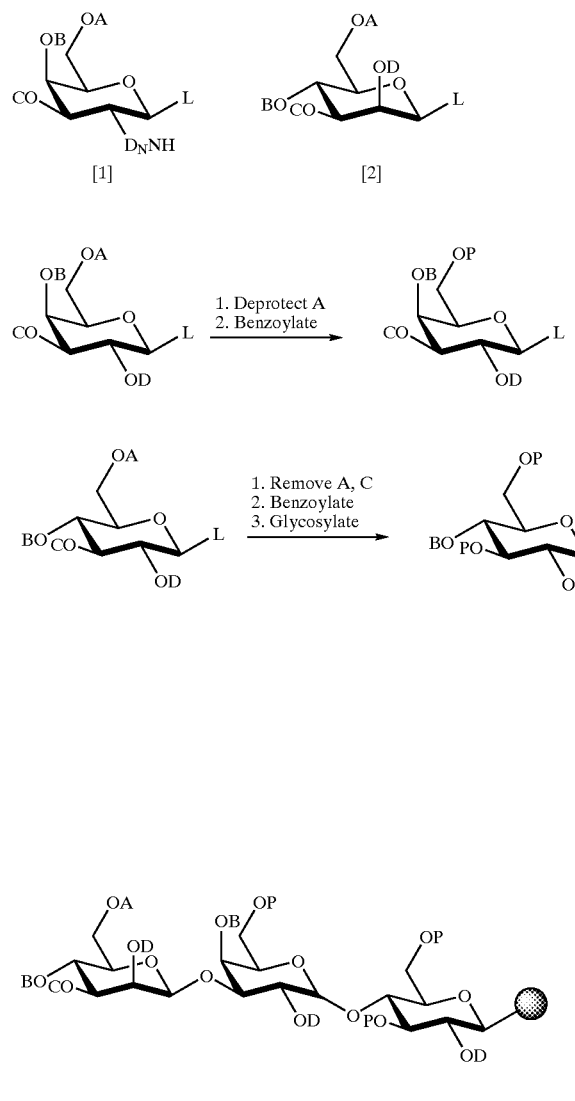
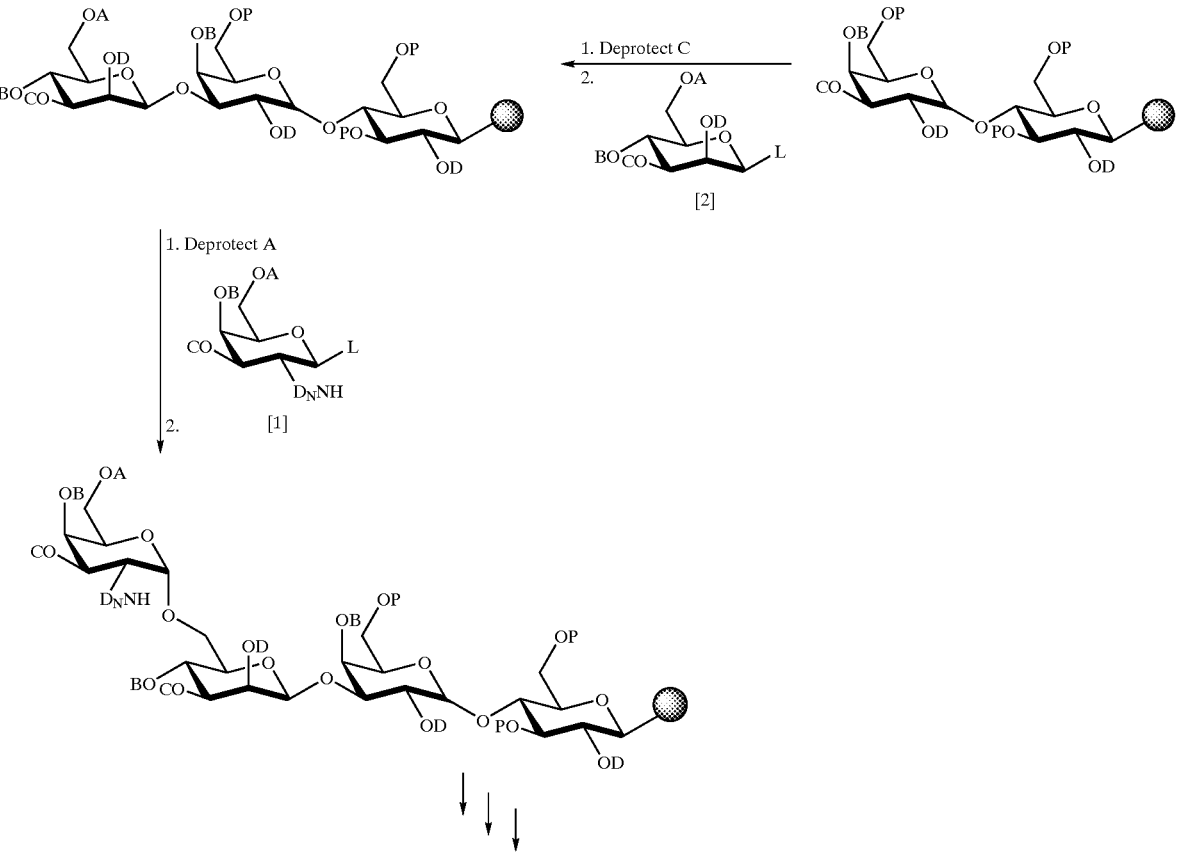

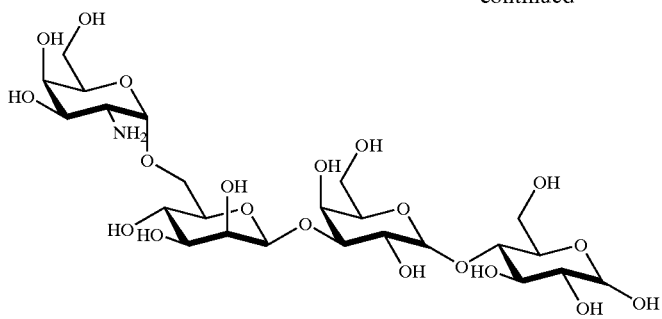

A–D = Orthogonal Hydroxy Protecting Groups
$D_N$ = Orthogonal Amino Protecting Group
P = Permanent Protecting Group (Benzoyl)
L = Activating Group In solution phase, protecting groups A and C from the first sugar residue of the target molecule (residue [4]) are selectively removed, and the sites capped by a permanent protecting group, eg. benzoyl group. The residue is then coupled to the resin, followed by selective removal of protecting group B. In solution phase, protecting group A from sugar residue [3] is selectively removed, and the site is capped by a permanent protecting group. Residue [3] is then linked to the resin-bound sugar residue via a glycosylation reaction. Protecting group C from the new disaccharide is removed, and residue [2] is linked via a glycosylation. Protecting group A is finally selectively removed to regenerate the 6-hydroxyl group, which is linked with residue 1.

EXAMPLE 2

Synthesis of an Orthogonally Protected Thioglycoside Building Block, Methyl 6-O-(t-butyldiphenylsilyl)-3-O-(p-chlorobenzoyl)-2-deoxy-2-[1-(4,4-dimethyl-2,6-dioxocyclohex-1-ylidene)ethylamino]-4-O-tetrahydropyranyl-1-thio-β-D Glucopyranoside (5)

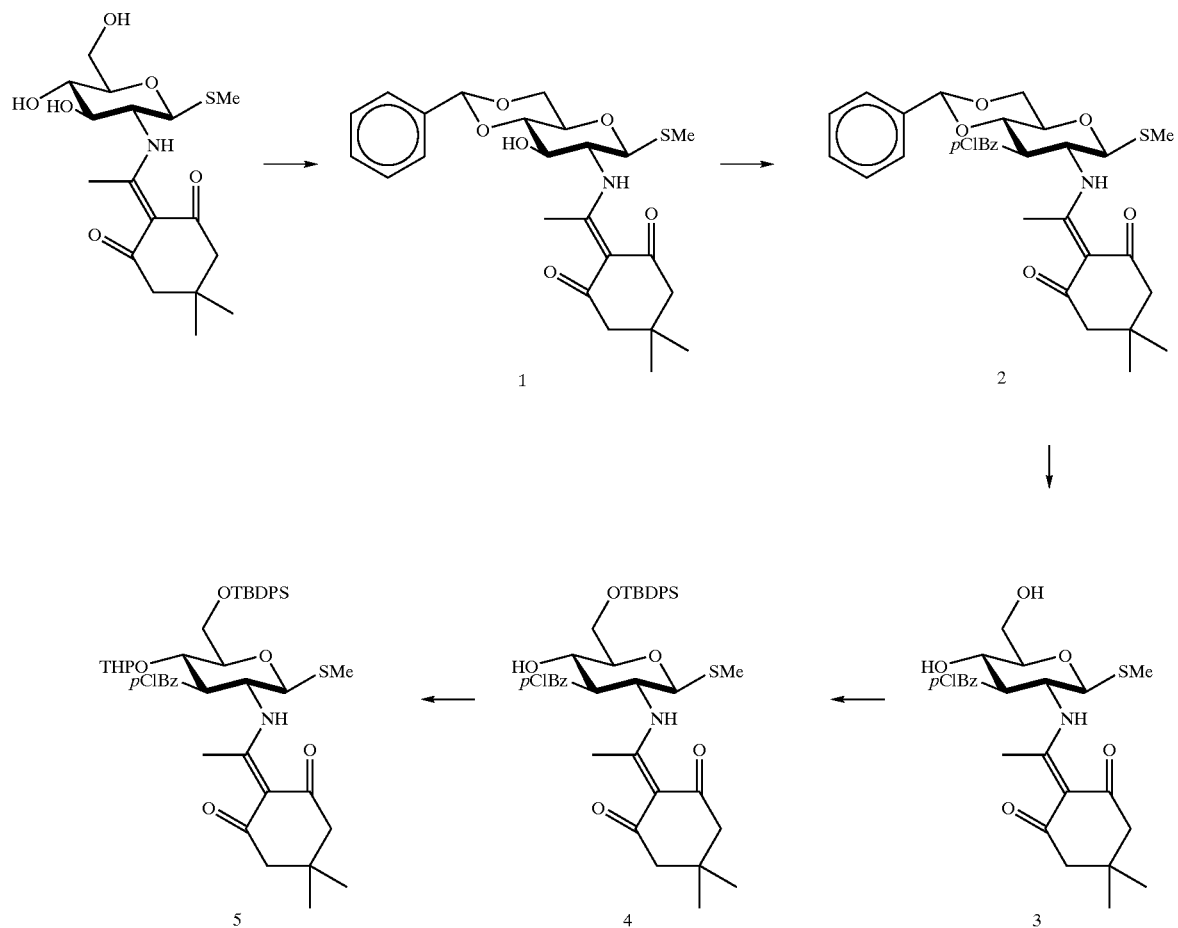

Methyl 4,6-O-benzylidene)-2-deoxy-2-[1-(4,4-dimethyl-2, 6dioxocyclohex-1-ylidene)ethylamino]-1-thio-β-D glucopyranoside (1)

A mixture of methyl 1-deoxy-2-[1-(4,4-dimethyl-2,6-dioxocyclohex-1-ylidene)ethylamino]-1-thio-62-D glucopyranoside (20 g, 54 mmol), α,α-dimethoxytoluene (9.78 g, 64 mmol) and p-toluenesulphonic acid (50 mg) in dry acetonitrile (100 mL), was stirred at 60° C. for 2 hours. The reaction mixture was cooled to room temperature and adjusted to pH 7 with the addition of triethylamine. The solvent was removed in vacuo, the residue was taken up in $CH_2Cl_2$ (200 ml), washed with brine (50 ml), with water (50 ml) and dried over $MgSO_4$. The organic phase was concentrated to give a yellow solid, methyl 4,6-O-benzylidine-2-deoxy-2-[1-(4,4-dimethyl-2,6-dioxocyclohex-1-ylidene)ethylamino]-1-thio-β-D glucopyranoside (24.5 g, 98%).

Methyl 4,6-O-benzylidene-3-O-(p-chlorobenzoyl)-2-deoxy-2-[1-(4,4-dimethyl-2,6-dioxocyclohex-1-ylidene)ethylamino]-1-thio-β-D glucopyranoside (2)

A mixture of methyl 4,6-O-benzylidene-2-deoxy-2-[1-(4, 4-dimethyl-2,6-dioxocyclohex-1-ylidene)ethylamino]-1-thio-β-D-glucopyranoside (1) (6.3 g, 13.5 mmol), p-chlorobenzoylchloride (2.6 ml, 20 mmol) and 4-dimethylaminopyridine (2.44 g, 40 mmol) in dry 1,2-dichloroethane (100 ml), was stirred at room temperature overnight. The resultant suspension was filtered, the filtrate diluted with chloroform (100 ml) and washed with diluted brine (3×50 ml, $H_2O$/Brine 2/1). The organic phase was dried over $MgSO_4$ and the solvent removed in vacuo to give yellow solid. The residue chromatographed EtOAc/Hexane 1:1 as the mobile phase to give methyl 4,6-O-benzylidene-3-O-(p-chlorobenzoyl)-2-deoxy-2-[1-(4,4-dimethyl-2,6-dioxocyclohex-1-ylidene)ethylamino]-1-thio-β-D-glucopyranoside (2) (6.4 g, 80%).

Methyl 3-O-(p-chlorobenzyl)-2-deoxy-2-[1-(4,4-dimethyl-2,6-dioxocyclohex-1-ylidene)ethylamino]-1-thio-62-D glucopyranoside (3)

A mixture of methyl 4,6-O-benzylidene-3-O-(p-chlorobenzoyl)-2-deoxy-2-[1-(4,4-dimethyl-2,6-dioxocyclohex-1-ylidene)ethylamino]-1-thio-β-D glucopyranoside (2) (2.51 g, 4.20 mmol) and 50% aqueous solution of tetrafluoroboric acid (1 ml) in acetonitrile (25 mL), was stirred at room temperature for 2 hours. The pH was adjusted to 7 with the addition of triethylamine and the resultant suspension concentrated. The residue was crystallised from diisopropyl ether-ethyl acetate to give methyl 3-O-(p-chlorobenzoyl)-2-deoxy-2-[1-(4,4-dimethyl-2,6-dioxocyclohex-1-ylidene)ethylamino]-1-thio-β-D glucopyranoside (3) (1.7 g, 79%).

Methyl 6-O-(t-butyldiphenylsilyl)-3-O-(p-chlorobenzoyl)-2-deoxy-2-[1-(4,4-dimethyl-2,6-dioxocyclohex-1-ylidene) ethylamino]-1-thio-β-D glucopyranoside (4)

A mixture of methyl 3-O-(p-chlorobenzoyl)-2-deoxy-2-[1-(4,4-dimethyl-2,6-dioxocyclohex-1-ylidene)-ethylamino]-1-thio-β-D-glucopyranoside (3) (1.00 g, 1.95 mmol), t-butyldiphenylsilylchloride (536 mg, 1.95) and 4-dimethylaminopyridine (238 mg, 1.95 mmol), in 1,2-dichloroethane (30 mL), was stirred under reflux for 6 hours. The reaction mixture was cooled to room temperature, diluted with chloroform (60 mL) and washed with diluted brine (3×50 mL, brine/water, 1:2), dried over $MgSO_4$. The solvent was removed in vacuo and the residue was chromatographed using hexane—EtOAc 1:1 as the mobile phase to give a white solid, methyl 6-O(t-butyldiphenylsilyl)-3-O-(p-chlorobenzoyl)-2-deoxy-2-[1-(4,4-dimethyl-2,6-dioxocyclohex-1-ylidene)ethylamino]-1-thio-β-D-glucopyranoside (4) (1.1 g, 75%).

Methyl 6-O-(t-butyldiphenylsilyl)-3-O-(p-chlorobenzoyl)-2-deoxy-2-[1-(4,4-dimethyl-2,6-dioxocyclohex-1-ylidene) ethylamino]-4-O-tetrahydropyranyl-1-thio-β-D glucopyranoside (5)

A mixture of methyl 6-O-(t-butyldiphenylsilyl)-3-O-(p-chlorobenzoyl)-2-deoxy-2-[1-(4,4-dimethyl-2,6-dioxocyclohex-1-ylidene)ethylamino]-1-thio-β-D-glucopyranoside (500 mg, 0.6 mmol), 3,4-dihydro-2H-pyran (5 mL) and -p-toluenesulphonic acid (5 mg) in dry acetonitrile (10 mL) was stirred at room temperature for 1 hour. The reaction mixture was adjusted to pH 7 with the addition of triethylamine and then evaporated to dryness. The residue was taken up in dichloromethane (30 mL), washed with water (2×10 mL) and the organic phase dried over $MgSO_4$. The solvent was removed in vacuo and the residue was chromatographed using hexane—EtOA 2:1 as the mobile phase to give methyl 6-O-(t-butyldiphenylsilyl)-3-O-(p-chlorobenoyl)-2-deoxy-2-[1-(4,4-dimethyl-2,6-dioxocyclohex-1-ylidene)ethylamino]-4-O-tetrahydropyranyl-1-thio-β-D-glucopyranoside (5) (420 mg, 85%).

EXAMPLE 3

Synthesis of an Orthogonally Protected Thioglycoside Building Block, Methyl 2-azido-6-O-(t-butyldiphenylsilyl)-2-deoxy-3- O-(4-methoxybenzyl)-4-O-biphenylcarbonyl-1-thio-β-D-glucopyranoside

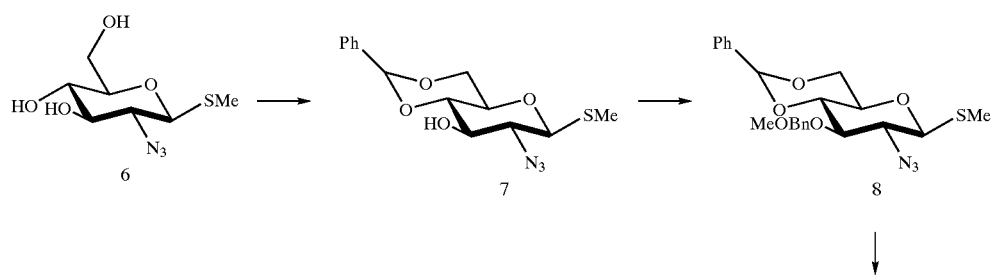

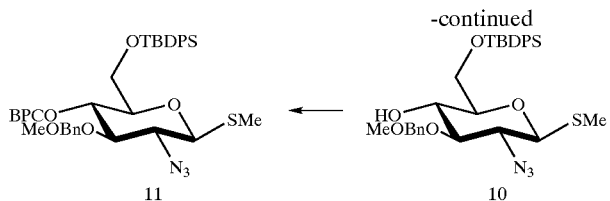

Methyl 2-azido-4,6-O-benzylidene-2-deoxy-1-thio-β-D glucopyranoside (7)

A mixture of methyl 2-azido-2-deoxy-1-thio-β-D glucopyranoside (6) 10 g, 4.25 mmol), α,α-dimethoxytoluene (9.71 g, 64 mmol) and p-toluenesulphonic acid (50 mg) in dry acetonitrile (100 mL), was stirred at 60° C. for 2 hours. The reaction mixture was cooled to room temperature and adjusted to pH 7 with the addition of triethylamine. The solvent was removed in vacuo. The residue was taken up in $CH_2Cl_2$ (200 mL), washed with brine (50 mL), with water (50 mL) and dried over $MgSO_4$. The organic phase was concentrated to give a white solid, methyl 2-azido-4,6-O-benzylidene-2-deoxy-1-thio-β-D glucopyranoside (7) (10.5 g, 73%).

Methyl 2-azido-4,6-O-benzylidene-2-deoxy-3-O-(4-methoxyphenyl)-1-thio-β-D glucopyranoside (8)

A suspension of sodium hydride (1.0 g, 41.8 mmol) in dry DMF (50 mL) was cooled to 0° C., and a solution of methyl 2-azido-4,6-O-benzylidene-2-deoxy-1-thio-β-D glucopyranoside (7) (9.0 g, 27.8 mmol) in dry DMF (50 mL) was added dropwise in 30 minutes. The resulting solution was stirred at 0° C. for 30 minutes and 4-methoxybenzyl chloride (6.54 g, 41.8 mmol) was added dropwise at 0° C. The reaction mixture was stirred at room temperature overnight, cooled to 0° C. and dry methanol (5 mL) was added dropwise. The reaction mixture was concentrated under reduced pressure, the xylene (50 mL) was co-evaporated from the residue. The residue was taken up in $CHCl_3$ (200 mL) washed with $H_2O$ (400 ml), saturated $NaHCO_3$ solution (200 mL) dried over $MgSO_4$ and evaporated to dryness. The residue was crystallized from EtOH to give methyl 2-azido-4,6-O-benzylidene-2-deoxy-3-O-(4-methoxybenzyl)-1-thio-β-D-glucopyranoside (8) (9,0 g, 73%) as white crystalline solid.

Methyl 2-azido-2-deoxy-3-O-(4-methoxybenzyl)-1-thio-β-D-glucopyranoside (9)

A mixture of methyl 2-azido-4,6-O-benzylidene-2-deoxy-3-O-(4-methoxybenzyl)-1-thio-β-D glucopyranoside (8) (12.0 g, 27.08 mmol) and p-toluenesulphonic acid (300 mg) in MeOH—MeCN 1:1 (400 mL) was stirred at 50° C. for 1 hour. The reaction mixture was evaporated, the residue was chromatographed using $CHCl_3$—EtOAc gradient to give methyl 2-azido-2-deoxy-3-O-(4-methoxybenzyl)-1-thio-62-D-glucopyranoside (9) (8.21 g, 88%).

Methyl 2-azido-6-O-tert-butyldiphenylsilyl-2-deoxy-3-O-(4-methoxybenzyl)-1-thio-β-D-glucopyranoside (10)

A mixture of t-butyldiphenylsilyl chloride (8.66 g, 31.53 mmol), 4-dimethylaminopyridine (5.12 g, 42.04 mmol) and methyl 2-azido-2-deoxy-3-O-(4-methoxybenzyl)-1-thio-β-D-glucopyranoside (9) (7.21 g, 21.02 mmol) in dry 1,2-dichloroethane (100 mL) was stirred at 80° C. for 2 hours. The resulting clear solution was cooled to room temperature, diluted with $CHCl_3$ (300 mL), washed with $H_2O$ (3×200 mL), brine solution (200 mL), dried over $MgSO_4$ and evaporated. The residue was purified by chromatography using hexane—ether 2:1 as the mobile phase to give methyl 2-azido-6-O-tert-butyldiphenylsilyl-2-deoxy-3-O-(4-methoxybenzyl-1-thio-β-D glucopyranoside (10) (9.73 g, 80%).

Methyl 2-azido-6-O-tert-butyldiphenylsilyl-4-O-biphenylcarbonyl-2-deoxy-3-O-(4-methoxyphenyl)-1-thio-β-D glucopyranoside (11)

A mixture of methyl 2-azido-6-O-tert-butyldiphenylsilyl-2-deoxy-3-O-(4-methoxybenzyl)-1-thio-β-D glucopyranoside (10) (12.7 g, 21.46 mmol), 4-dimethylaminopyridine (5.23 g, 42.92 mmol) in dry 1,2-dichloroethane (100 mL) was stirred at room temperature. Biphenylcarbonyl chloride (6.97 g, 32.19 mmol) was added to the stirred reaction mixture in 15 minutes. After the addition the resulting suspension was stirred under reflux for 3 hours. The reaction mixture was cooled to 10° C. and filtered. The crystalline solid was washed on the funnel with dry 1,2-dichloroethane (50 mL) and filtered. The filtrates were combined, diluted with $CHCl_3$ (200 mL) and washed twice with diluted brine solution (water-brine 2:1) (150 mL). The organic layer was dried over $MgSO_4$ and evaporated. The residue was crystallized from EtOH (75 mL) to give methyl 2-azido-6-O-tert-butyldiphenylsilyl-4-O-biphenylcarbonyl-2-deoxy-3-O-(4-methoxybenzyl)-1-thio-β-D-glucopyranoside (11) (12.7 g, 76%)

EXAMPLE 4

Synthesis of an Orthogonally Protected Thioglycoside Building Block, Methyl 2-azido-6-O-(t-butyldiphenylsilyl)-2-deoxy-3-O-(4-methoxybenzyl)-4-O-biphenylcarbonyl-1-thio-β-D-galactopyranoside (17)

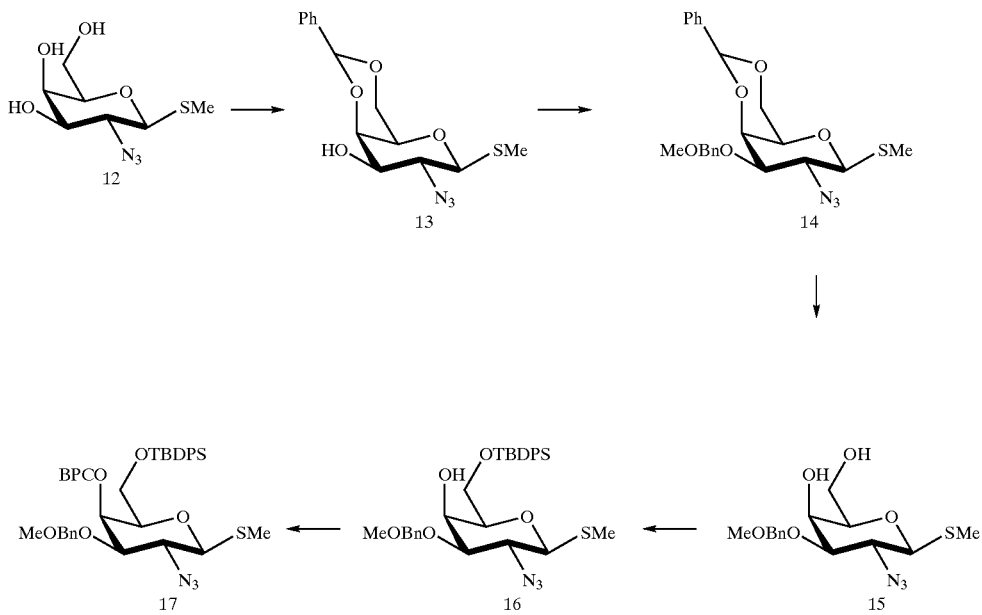

Methyl 2-azido-4,6-O-benzylidene-2-deoxy-1-thio-β-D galactopyranoside (13)

A mixture of methyl 2-azido-2-deoxy-1-thio-β-D-galactopyranoside (12) (3.0 g, 12.76 mmol), α,α-dimethoxytoluene (2.91 g, 19.14 mmol) and p-toluenesulphonic acid (30 mg) in dry acetonitrile (15 mL), was stirred at 70° C. for 20 minutes. The reaction mixture was cooled to room temperature and adjusted to pH 7 with the addition of triethylamine. The solvent was removed in vacuo and the residue was taken up in CH$_2$Cl$_2$ (100 mL), washed with brine (50 mL), with water (50 mL) and dried over MgSO$_4$. The organic phase was concentrated to give a white solid, methyl 2-azido-4,6-O-benzylidene-2-deoxy-1-thio-β-D-galactopyranoside (13) (3.09 g, 75%).

Methyl 2-azido-4,6-O-benzylidene-2-deoxy-3-O-(4-methoxybenzyl)-1-thio-β-D-galactopyranoside (14)

A suspension of sodium hydride (123 mg, 4.87 mmol) in dry DMF (10 mL) was cooled to 0° C., and a solution of methyl 2-azido-4,6-O-benzylidene-2-deoxy-1-thio-β-D-galactopyranoside (13) (1.05 g, 3.25 mmol) in dry DMF (10 mL) was added dropwise in 30 minutes. The resulting solution was stirred at 0° C. for 30 minutes and 4-methoxybenzyl chloride (763 mg, 4.87 mmol) was added dropwise at 0° C. The reaction mixture was stirred at room temperature overnight, cooled to 0° C. and dry methanol (2-mL) was added dropwise. The reaction mixture was concentrated under reduced pressure, then xylene (25 mL) was co-evaporated from the residue. The residue was taken up in CHCl$_3$ (50 mL) washed with H$_2$O (40 ml), saturated NaHCO$_3$ solution (50 mL) dried over MgSO$_4$ and evaporated to dryness. The residue was crystallized from EtOH (10 mL) to give methyl 2-azido-4,6-O-benzylidene-2-deoxy-3-O-(4-methoxybenzyl)-1-thio-β-D-galactopyranoside (14) (1.0 g, 70%) as white crystalline solid.

Methyl 2-azido-2-deoxy-3-O-(4-methoxybenzyl)-1-thio-β-D-galactopyranoside (15)

A mixture of methyl 2-azido-4,6-O-benzylidene-2-deoxy-3-O-(4-methoxybenzyl)-1-thio-β-D-galactopyranoside (14) (500 mg, 1.12 mmol) and p-toluenesulphonic acid (10 mg) in MeOH—MeCN 1:1 (50 mL) was stirred at 50° C. for 1 hour. The reaction mixture was evaporated, the residue was chromatographed using CHCl3—EtOAc gradient to give methyl 2-azido-2-deoxy-3-O-(4-methoxybenzyl)-1-thio-β-D-galactopyranoside (15) (309 mg, 80%)

Methyl 2-azido-6-O-tert-butyldiphenylsilyl-2-deoxy-3-O-(4-methoxybenzyl)-1-thio-β-D-galactopyranoside (16)

A mixture of t-butyldiphenylsilyl chloride (151 mg, 0.54 mmol), 4-dimethylaminopyridine (90 mg, 0.73 mmol) and methyl 2-azido-2-deoxy-3-O-(4-methoxybenzyl)-1-thio-β-D-galactopyranoside (15) (130 mg, 0.36 mmol) in dry 1,2-dichloroethane (8 mL) was stirred at 80° C. for 2 hours. The resulting clear solution was cooled to room temperature, diluted with CHCl$_3$ (20 mL), washed with H$_2$O (3×20 mL), brine solution (20 mL), dried over MgSO$_4$ and evaporated. The residue was purified by chromatography using hexane—ether 2:1 as the mobile phase to give methyl 2-azido-6-O-tert-butyldiphenylsilyl-2-deoxy-3-O-(4-methoxybenzyl)-1-thio-β-D-galactopyranoside (16) (142 mg, 68%).

Methyl 2-azido-6-O-tert-butyldiphenylsilyl-4-O-biphenylcarbonyl-2-deoxy-3-O-(4-methoxybenzyl)-1-thio-β-D-galactopyranoside (17)

A mixture of methyl 2-azido-6-O-tert-butyldiphenylsilyl-2-deoxy-3-O-(4-methoxybenzyl)-1-thio-β-D-galactopyranoside (16) (213 mg, 0.36 mmol), 4-dimethylaminopyridine (67 mg, 0.55 mmol) in dry 1,2-dichloroethane (10 mL) was stirred at room temperature. Biphenylcarbonyl chloride (119 mg, 0.55 mmol) was added to the stirred reaction mixture. The resulting suspension was stirred under reflux for 3 hours. The reaction mixture was cooled to 10° C. and filtered. The crystalline solid was washed on the funnel with dry 1,2-dichloroethane (5 mL) and filtered. The filtrates were combined, diluted with CHCl₃ (20 mL) and washed twice with diluted brine solution (water-brine 2:1) (15 mL). The organic layer was dried over MgSO₄ and evaporated. The residue was purified by chromatography using hexane—CHCl₃ 1:1 as the mobile phase to give methyl 2-azido-6-O-tert-butyldiphenylsilyl-4-O-biphenylcarbonyl-2-deoxy-3-O-(4-methoxybenzyl)-1-thio-β-D-galactopyranoside (17) (18mg, 65%).

EXAMPLE 5

Synthesis of an Orthogonally Protected Thioglycoside Building Block, Methyl 6-O-(t-butyldiphenylsilyl)-2-deoxy-2-[(1,3-dimethyl-2,4,6 (1H,3H,5H)-trioxopyrimidin-5-ylidene) methylamino]-3-O-(4-methoxybenzyl)-4-O-biphenylcarbonyl-1-thio-β-D-glucopyranoside (24).

5H)-trioxopyrimidine (Wow-reagent) (62.27 g, 294.9 mmol) in hot MeOH (120 mL) was added. /Synthesis of 1,3-Dimethyl-5-[(dimethylamino)methylene]2,4,6 (1H, 3H, 5H)- trioxopyrimidine (Wow-reagent): N,N-Dimethylformamide dimethyl acetal (252 g, 2.11 mol) was stirred at 0° C. in CHCl₃ (750 mL). 1,3-Dimethylbarbituric acid (300 g, 1.92 mol) in CHCl₃ (2100 mL) was added to the stirring acetal solution over 2 hours. The CHCl₃ was evaporated immediately following complete addition and the resulting residue re-suspended in GHCl₃ (2000 mL) and washed with water (3×600 mL) and saturated brine solution (600 mL). The organic phase was dried over MgSO₄, filtered and evaporated to dryness under high vacuum. The residue was re-suspended in diethyl ether (750 mL), filtered and washed on the funnel with additional diethyl ether (500 mL) to yield 1,3-Dimethyl-5-[(dimethylamino)methylene]2,4,6 (1H,3H,5H)-trioxopyrimidine as a pale-yellow solid (271.85

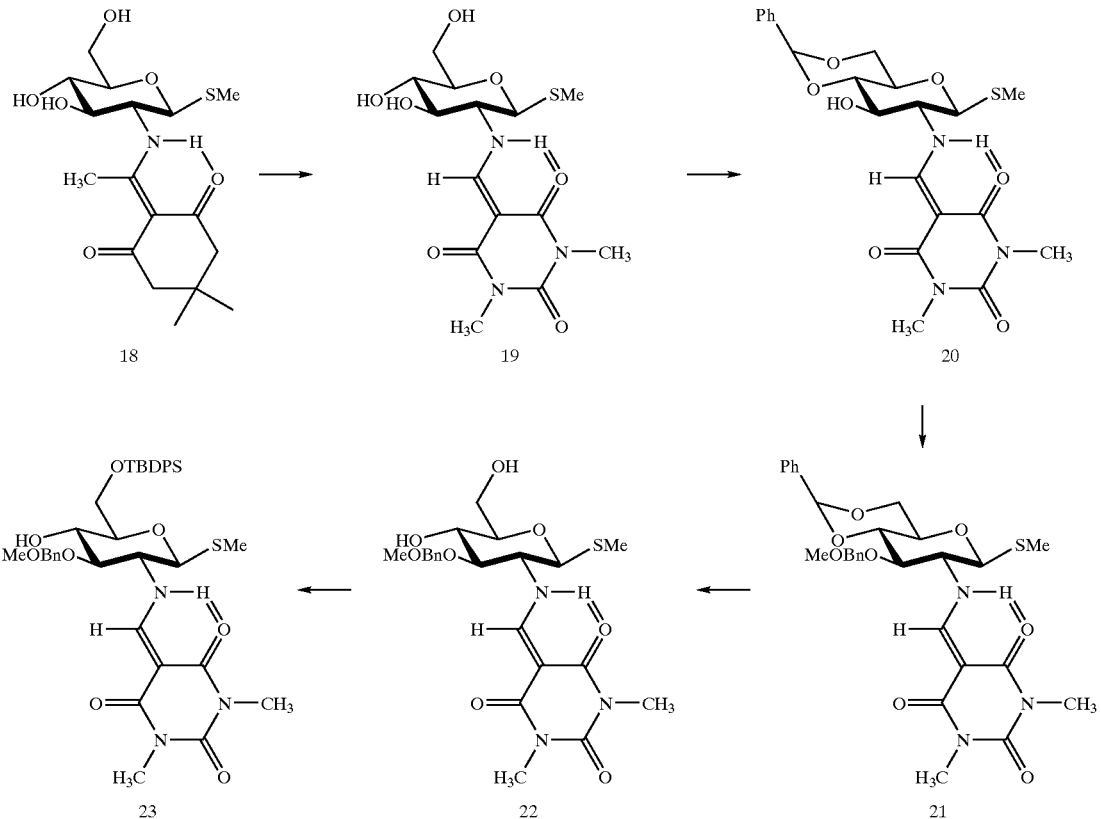

Methyl 2-deoxy-2-[(1,3-dimethyl-2,4,6(1H,3H,5H)-trioxopyrimidin-5-ylidene)methylamino]-1-thio-β-D-glucopyranoside (19)

To methyl 2-deoxy-2-[1-(4,4-dimethyl-2,6-dioxocyclohex-1-ylidene)-ethylamino]-1-thio-β-D-glucopyranoside (18) (100 g, 268 mmol) was added conc. ammonia solution (300 mL) and the reaction mixture was stirred at 100° C. for 1 hour. The suspension was cooled to room temperature and filtered. The filtrate was washed with CHCl₃ (3×200 mL), then the aqueous phase was evaporated under reduced pressure. The residue was taken up in EtOH:benzene 1:1 (250 mL) and evaporated to dryness.

The residue was taken up in hot MeOH (600 mL) and 1,3-dimethyl-5-[(dimethylamino)methylene]2,4,6(1H,3H, g, 67%)./ The reaction mixture was stirred under reflux for 30 minutes, then cooled to room temperature. The resulting suspension was filtered, the solid was washed with MeOH (150 mL), ether (150 mL), dried to give methyl 2-deoxy-2-[(1,3-dimethyl-2,4,6(1H,3H,5H)-trioxopyrimidin-5-ylidene)methylamino]-1-thio-β-D-glucopyranoside (19) (83 g, 90%).

Methyl 4,6-O-benzylidene-2-deoxy-2-[(1,3-dimethyl-2,4,6 (1H,3H,5H)-trioxopyrimidin-5-ylidene)methylamino]-1-thio-β-D-glucopyranoside (20)

A mixture of methyl 2-deoxy-2-[(1,3-dimethyl-2,4,6(1H, 3H,5H)-trioxopyrimidin-5-ylidene)methylamino]-1-thio-β-D-glucopyranoside (19) (84.64 g, 226.31 mmol), α,α-dimethoxytoluene (55.66 g, 339.46 mmol) and p-toluenesulphonic acid (500 mg) in dry acetonitrile (600 mL), was stirred at 60° C. for 2 hours. The reaction mixture was cooled to room temperature and filtered. The solid was washed with ether (200 mL), dried to give methyl 4,6-O-benzylidene-2-deoxy-[1,3-dimethyl-2,4,6-(1H,3H,5H)-trioxopyrimidin-5-ylidene)methylamino]-1-thiol-β-D-glucopyranoside (20) (80 g, 77%).

Methyl 4,6-O-benzylidene-2-deoxy-2-[1,3-dimethyl-2,4,6 (1H,3H,5H)-trioxopyrimidin-5-ylidene)methylamino]-3-O-(4-methoxybenzyl)-1-thio-β-D-glucopyranoside (21)

A suspension of sodium hydride (6.82 g, 269.97 mmol) in dry DMF (50 mL) was cooled to 0° C., and a solution of methyl 4,6-O-benzylidene-2-deoxy-2-[(1,3-dimethyl-2,4,6 (1H,3H,5H)-trioxopyrimidin-5-ylidene)methylamino]-1-thio-β-D-glucopyranoside (20) (50 g, 107.99 mmol in dry DMF (200 mL) was added dropwise in 30 minutes. The resulting solution was stirred at room temperature for 30 minutes and 4-methoxybenzyl chloride (37.36 g, 238.56 mmol) was added dropwise at 0° C. The reaction mixture was stirred at room temperature overnight, cooled to 0° C. and dry methanol (10 mL) was added dropwise. The reaction mixture was concentrated under reduced pressure, then xylene (200 mL) was co-evaporated from the residue. The residue was taken up in CHCl₃ (1000 mL) washed with H₂O (1000 ml), saturated NaHCO₃ solution (1000 mL) dried over MgSO₄ and evaporated to dryness. The residue was crystallized from EtOH to give methyl 4,6-O-benzylidene-2-deoxy-2-[(1,3-dimethyl-2,4,6(1H,3H,5H)-trioxopyrimidin-5-ylidene)methylamino]-3-O-(4-methoxybenzyl)-1-thio-β-D-glucopyranoside (21) (52.21 g, 82%).

Methyl 2-deoxy-2-[1,3-dimethyl-2,4,6(1H,3H,5H)-trioxopyrimidin-5-ylidene)methylamino]-3-O-(4-methoxybenzyl)-1-thio-β-D-glucopyranoside (22)

A mixture of methyl 4,6-O-benzylidene-2-deoxy-2-[(1,3-dimethyl-2,4,6(1H,3H,5H)-trioxopyrimidin-5-ylidene) methylamino]-3-O-(4-methoxybenzyl)-1-thio-β-D-glucopyranoside (21) (52.21 g, 89.55 mmol and p-toluenesulphonic acid (200 mg) in MeOH—MeCN 1:1 (400 mL) was stirred at 50° C. for 1 hour. The reaction mixture was evaporated, the residue was chromatographed using CHC13—MeOH 10:1 as the mobile phase to give methyl 2-deoxy-2-[(1,3-dimethyl-2,4,6(1H,3H,5H)-trioxopyrimidin-5-ylidene)methylamino]-3-O-(4-methoxybenzyl)-1-thio-β-D-glucopyranoside (22) (31.0 g, 70%)

Methyl 6-O-tert-butyldiphenylsilyl-2-deoxy-2-[(1,3-dimethyl-2,4,6(1H,3H,5H)-trioxopyrimidin-5-ylidene) methylamino]-3-O-(4-methoxybenzyl)-1-thio-β-D-glucopyranoside (23)

A mixture of t-butyldiphenylsilyl chloride (16.65 g, 60.60 mmol), 4-dimethylaminopyridine (9.85 g, 80.80 mmol) and methyl 2-deoxy-2-[1,3-dimethyl-2,4,6-(1H,3H,5H)-trioxopyrimidin-5-ylidene)methylamino]-3-O-(4-methoxybenzyl)-1-thio-β-D-glucopyranoside (22) (20 g, 40.4 mmol) in dry 1,2-dichloroethane (200 mL) was stirred at 80° C. for 2 hours. The resulting clear solution was cooled to room temperature, diluted with CHCl₃ (200 mL), washed with H₂O (3×500 mL), brine solution (500 mL), dried over MgSO₄ and evaporated. The residue was purified by chromatography using 1,2-dichloroethane—EtOAc 10:1 as the mobile phase to give methyl 6-O-tert-butyldiphenylsilyl-2-deoxy-2-[(1,3-dimethyl-2,4,6(1H,3H,5H)-trioxopyrimidin-5-ylidene)methylamino]-3-O-(4-methoxybenzyl)-1-thio-β-D-glucopyranoside (23) (23.3 g, 79%).

Methyl 6-O-tert-butyldiphenylsilyl-4-O-biphenylcarbonyl-2-deoxy-2-[(1,3-dimethyl-2,4,6(1H,3H,5H)-trioxopyrimidin-5-ylidene)methylamino]-3-O-(4-methoxybenzyl)-1-thio-β-D-glucopyranoside (24)

A mixture of methyl 6-O-tert-butyldiphenylsilyl-2-deoxy-2-[(1,3-dimethyl-2,4,6-(1H,3H,5H)-trioxopyrimidin-5-ylidene)methylamino]-3-O-(4-methoxybenzyl)-1-thio-β-D-glucopyranoside (23) (10.0 g, 13.64 mmol), 4-dimethylaminopyridine (2.5 g, 20.46 mmol) in dry 1,2-dichloroethane (100 mL) was stirred at room temperature. Biphenylcarbonyl chloride (4.42 g, 20.46 mmol) was added to the stirred reaction mixture. The resulting suspension was stirred under reflux for 3 hours. The reaction mixture was cooled to 10° C. and filtered. The crystalline solid was washed on the funnel with dry 1,2-dichloroethane (20 mL) and filtered. The filtrates were combined, diluted with CHCl₃ (100 mL) and washed twice with diluted brine solution (water-brine 2:1) (150 mL). The organic layer was dried over MgSO₄ and evaporated. The residue was purified by chromatography using hexane—CHCl₃ 1:1 as the mobile phase to give methyl 6-O-tert-butyldiphenylsilyl-4-O-biphenylcarbonyl-2-deoxy-2-[(1,3-dimethyl-2,4,6(1H,3H,5H)-trioxopyrimidin-5-ylidene)methylamino]-3-O-(4-methoxybenzyl-1-thio-β-D-glucopyranoside (24) (9.5 g, 75%).

EXAMPLE 6

Synthesis of an Orthogonally Protected Thioglycoside Building Block, Methyl 6-O-(t-butyldiphenylsilyl)-2-O-(4-methoxybenzyl)-3-O-allyl-4-O-acetyl-1-thio-β-D-galactopyranoside (31)

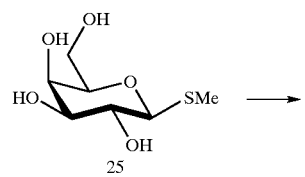 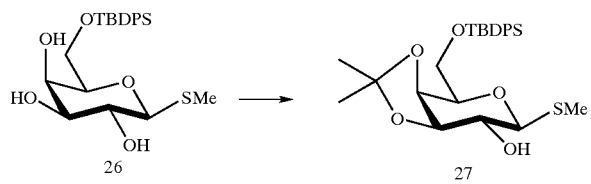

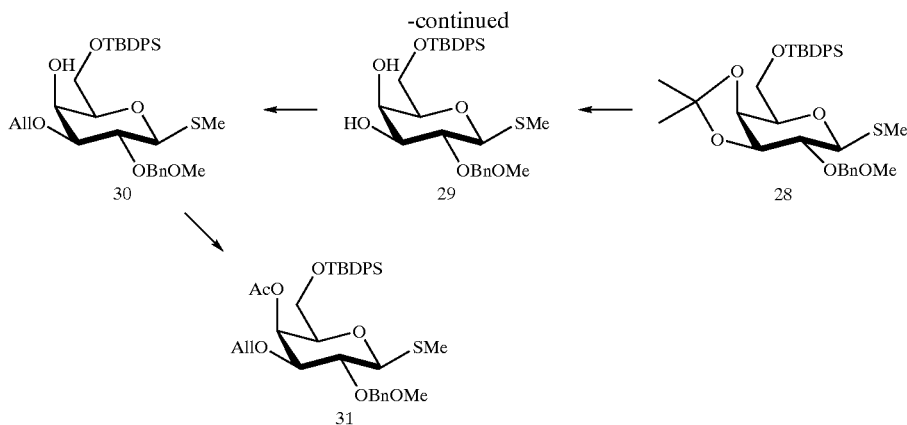

Methyl 6-O-(t-butyldiphenylsilyl)-1-thio-β-D-galactopyranoside (26)

A mixture of methyl 1-thio-β-D-galactopyranoside (25) 5 g, 28 mmol), chloro t-butyldiphenylsilane (5.85 g, 21 mmol) and DMAP (2.63 g, 21 mmol) in dry 1,2-dichloroethane (130 mL) was left to stir at reflux for 2.5 h. The reaction mixture was cooled to room temperature, diluted with dichloromethane (200 mL) and washed with saturated sodium chloride solution (2×250 mL). The organic phase was dried over MgSO$_4$ and subsequently evaporated to dryness to give methyl 6-O-(t-butyldiphenylsilyl)-1-thio-β-D-galactopyranoside (26) (7.5 g, 81%) as a colorless oil.

Methyl 6-O-(t-butyldiphenylsilyl)-3,4-O-isopropylidene-1-thio-β-D-galactopyranoside (27)

A mixture of methyl 6-O-(t-butyldiphenylsilyl)-1-thio-β-D-galactopyranoside (26) (7.4 g, 16.5 mmol) and p-toluenesulphonic acid (20 mg) in 2,2-dimethoxypropane (100 mL) was left to stir at room temperature for 2 h. The reaction mixture was then neutralized with triethylamine (1 mL) and evaporated to dryness. The residue was dissolved in dichloromethane (250 mL), washed with water (1×250 mL), dried over MgSO$_4$ and evaporated to dryness to give methyl 6-O-(t-butyldiphenylsilyl)-3,4-O-isopropylidene-1-thio-β-D-galactopyranoside (27) (7.0 g, 87%) as a white solid.

Methyl 6-O-(t-butyldiphenylsilyl)-2-O-(4-methoxybenzyl)-3,4-O-isopropylidene-1-thio-β-D-galactopyranoside (28)

To a suspension of sodium hydride (95%, 0.53 g, 21 mmol) in dry DMF (100 mL) at 0° C., was added dropwise methyl 6-O-(t-butyldiphenylsilyl)-3,4-O-isopropylidene-1-thio-β-D-galactopyranoside (27) (6.8 g, 13.9 mmol) as a solution in dry DMF (25 mL) in 5 minutes. The resulting mixture was left to stir at 0° C. for 15 min and then at room temperature for 1 h. The mixture was then cooled to 0° C. and a solution of 4-methoxybenzyl chloride (3.27 g, 21 mmol) in dry DMF (25 mL) was added dropwise, over 5 min. The reaction mixture was left to stir at 0° C. for 15 min and then at room temperature for 16 h. After this period the reaction was neutralized with absolute ethanol (15 mL) at 0° C. and then evaporated to dryness. The residue was taken up in chloroform (400 mL), washed with water (300 mL) and saturated sodium bicarbonate solution (300 mL). The organic phase was dried over MgSO$_4$ and evaporated to dryness to give the crude product as an orange oil (~9 g). The crude material was chromatographed using EtOAc—hexane 25:75 as the mobile phase to give methyl 6-O-(t-butyldiphenylsilyl)-2-O-(4-methoxybenzyl)-3,4-O-isopropylidene-1-thio-β-D-galactopyranoside (28) as a pale yellow oil (6.5 g, 77%).

Methyl 6-O-(t-butyldiphenylsilyl)-2-O-(4-methoxybenzyl)-1-thio-β-D-galactopyranoside (29)

A suspension of methyl 6-O-(t-butyldiphenylsilyl)-2-O-(4-methoxybenzyl)-3,4-O-isopropylidene-1-thio-β-D-galactopyranoside (28) (6.4 g, 10.5 mmol) in acetic acid (80%, 150 mL) was left to stir at 70° C. for 1.5 h. The reaction mixture was evaporated to dryness and the remaining residue was chromatographed using EtOAc-hexane 1:1) to give methyl 6-O-(t-butyldiphenylsilyl)-2-O-(4-methoxybenzyl)-1-thio-β-D-galactopyranoside (29) as a pale yellow oil (3.0 g, 50%).

Methyl 6-O-(t-butyldiphenylsilyl)-2-O-(4-methoxybenzyl)-3-O-allyl-1-thio-β-D-galactopyranoside (30)

A mixture of methyl 6-O-(t-butyldiphenylsilyl)-2-O-(4-methoxybenzyl)-1-thio-β-D-galactopyranoside (29) (2.8 g, 4.9 mmol) and dibutyl tin oxide (1.6 g, 6.4 mmol) in anhydrous methanol (200 mL) was stirred at reflux for 1 h. The reaction mixture was evaporated to dryness and the remaining residue dissolved in dry toluene (50 mL). Tetraethylammonium bromide (1.34 g, 6.4 mmol) and allyl bromide (7.7 g, 64 mmol) were added. The reaction mixture was left to stir at reflux overnight. The reaction mixture was cooled to room temperature and filtered. The filtrate was evaporated to dryness and the residue was purified by chromatography using EtOAc—hexane 15:85 as the mobile phase to give methyl 6-O-(t-butyldiphenylphenylsilyl)-2-O-(4-methoxybenzyl)-3-O-allyl-1-thio-β-D-galactopyranoside (30) (1.5 g, 50%) as a pale yellow oil.

Methyl 6-O-(t-butyldiphenylsilyl)-2-O-(4-methoxybenzyl)-3-O-allyl-4-O-acetyl-1-thio-β-D-galactopyranoside (31)

To a solution of methyl 6-O-(t-butyldiphenylsilyl)-2-O-(4-methoxybenzyl)-3-O-allyl-1-thio-β-D-galactopyranosidee (30) (1.4 g, 2.3 mmol) in pyridine (30 mL) was added acetic anhydride (20 g, 196 mmol) in one portion. The resulting solution was left to stir at room temperature for 72 h. The reaction contents were then evaporated to dryness and there residue was dissolved in dichloromethane (200 mL). The solution was washed with potassium hydrogen sulphate solution (1 M×2×50 mL) followed by saturated sodium chloride (150 mL), dried over MgSO$_4$ and evaporated to dryness. The crude residue was purified by chromatography using dichloromethane as the mobile phase to give Methyl 6-O-(t-butyldiphenylsilyl)-2-O-(4-methoxybenzyl)-3-O-allyl-4-O-acetyl-1-thio-β-D-galactopyranoside (31)(750 mg, 48%) as a pale yellow oil.

EXAMPLE 7

Selective Deprotection—Etherification Study Using an Orthogonally Protected Thioglycoside Building Block, Methyl 2-azido-6-O-tert-butyldiphenylsilyl-4-O-biphenylcarbonyl-2-deoxy-3-O-(4-methoxybenzyl)-1-thio-β-D-glucopyranoside (11)

Methyl 2-azido-6-O-tert-butyldiphenylsilyl-2-deoxy-3-O-(4-methoxyphenyl)-1-thio-β-D-glucopyranoside (10)

Sodium (89 mg) was reacted in dry MeOH (50 mL) then a solution of methyl 2-azido-4-O-biphenylcarbonyl-6-O-tert-butyldiphenylsilyl-2-deoxy-3-O-(4-methoxybenzyl)-1-thio-β-D-glucopyranoside (11) (3 g, 3.88 mmol) in THF (25 mL) was added. The reaction mixture was stirred at 40° C. for 30 minutes, then cooled to room temperature. The solution was neutralized by Amberlite IR 120 (H$^+$) ion exchange resin. The suspension was filtered, the filtrate was evaporated. The residue was purified by chromatography using EtOAc—hexane 1:4 as the mobile phase to give

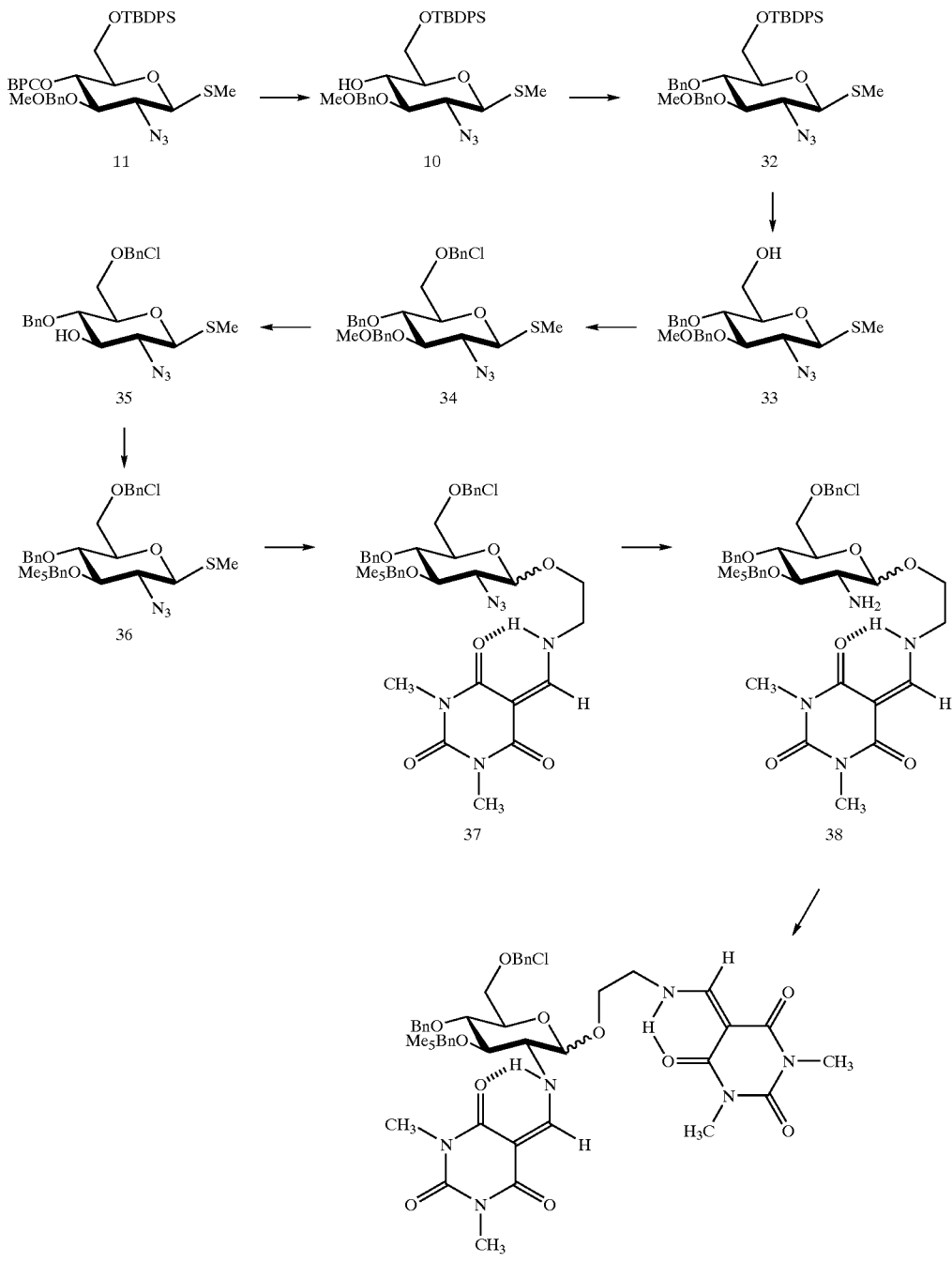

methyl 2-azido-6-O-tert-butyldiphenylsilyl-2-deoxy-3-O-(4-methoxybenzyl)-1-thio-β-D-glucopyranoside (10) (2.1 g, 91%)

Methyl 2-azido-4-O-benzyl-6-O-tert-butyldiphenylsilyl-2-deoxy-3-O-(4-methoxybenzyl)-1-thio-β-D-glucopyranoside (32)

A suspension of sodium hydride (196 mg, 5.1 mmol) in dry DMF (10 mL) was cooled to 0° C., and a solution of methyl 2-azido-6-O-tert-butyldiphenylsilyl-2-deoxy-3-O-(4-methoxybenzyl)-1-thio-β-D glucopyranoside (10) (2.53 g, 4.3 mmol) in dry DMF (20 mL) was added dropwise in 30 minutes. The resulting solution was stirred at room temperature for 30 minutes and benzyl bromide (880 mg, 5.1 mmol) was added dropwise at 0° C. The reaction mixture was stirred at room temperature overnight, cooled to 0° C. and dry methanol (1 mL) was added dropwise. The reaction mixture was concentrated under reduced pressure, then xylene (20 mL) was co-evaporated from the residue. The residue was taken up in $CHCl_3$ (100 mL) washed with $H_2O$ (100 ml), saturated $NaHCO_2$ solution (100 mL) dried over $MgSO_4$ and evaporated to dryness. The residue was purified by chromatography using EtOAc—Hexane 1:9 as the mobile phase to give methyl 2-azido-4-O-benzyl-6-O-tert-butyldiphenylsilyl-2-deoxy-3-O-(4-methoxybenzyl)-1-thio-β-D-glucopyranoside (32) (2.0 g, 68%).

Methyl 2-azido-4-O-benzyl-2-deoxy-3-O-(4-methoxybenzyl)-1-thio-β-D-glucopyranoside (33)

To a mixture of methyl 2-azido-4-O-benzyl-6-O-tert-butyldiphenylsilyl-2-deoxy-3-O-(4-methoxybenzyl)-1-thio-β-D-glucopyranoside (32) (1.5 g, 2.2 mmol) and anhydrous AcOH (28.8 mL) in dry THF (169 mL) hydrogen fluoride-pyridine complex (20.3 mL) was added in a polypropylene container. The reaction mixture was kept at room temperature overnight, then diluted with EtOAc (1 L). The resulting solution was washed with saturated sodium hydrogen carbonate (4×1 L), saturated brine solution (1 L), dried over $MgSO_4$ and evaporated to dryness. The residue was crystallized from MeOH. The mother liquor was evaporated, the residue was treated with hexane to get more solid. The solid products were combined affording methyl 2-azido-4-O-benzyl-2-deoxy-3-O-(4-methoxybenzyl)-1-thio-β-D-glucopyranoside (33) (735 mg, 75%).

Methyl 2-azido-4-O-benzyl-6-O-(4-chlorobenzyl)-2-deoxy-3-O-(4-methoxybenzyl)-1-thio-β-glucopyranoside (34)

A suspension of sodium hydride (71 mg, 1.8 mmol) in dry DMF (5 mL) was cooled to 0° C., and a solution of methyl 2-azido-4-O-benzyl-2-deoxy-3-O-(4-methoxybenzyl)-1-thio-β-D-glucopyranoside (33) (680 mg, 1.5 mmol) in dry DMF (5 mL) was added dropwise in 30 minutes. The resulting solution was stirred at room temperature for 30 minutes and 4-chlorobenzyl chloride (295 mg, 1.5 mmol) was added dropwise at 0° C. The reaction mixture was stirred at room temperature for 4.5 hours, cooled at 0° C. and dry methanol (1 mL) was added dropwise. The reaction mixture was concentrated under reduced pressure, then xylene (10 mL) was co-evaporated from the residue. The residue was treated with hexane (10 mL) and filtered to give methyl 2-azido-4-O-benzyl-6-O-(4-chlorobenzyl)-2-deoxy-3-O-(4-methoxybenzyl)-1-thio-β-D-glucopyranoside (34) (620 mg, 71%).

Methyl 2-azido-4-O-benzyl-6-O-(4-chlorobenzyl)-2-deoxy-1-thio-β-D-glucopyranoside (35)

A mixture of methyl 2-azido-4-O-benzyl-6-O-(4-chlorobenzyl)-2-deoxy-3-O-(4-methoxybenzyl)-1-thio-β-D glucopyranoside (34) (580 mg, 1.01 mmol) and DDQ (270 mg, 1.2 mmol) in $CH_2Cl_2$—$H_2O$ 9:1 (10 mL) was stirred at room temperature for 3 hours. The reaction mixture was washed with saturated $NaHCO_3$ solution (3×15 ml), dried over $MgSO_4$ and evaporated. The residue was purified by chromatography using $CHCl_3$-Hexane-MeOH 30:20:0.5 as the mobile phase to give methyl 2-azido-4-O-benzyl-6-O-(4-chlorobenzyl)-2-deoxy-1-thio-β-D glucopyranoside (35) (300 mg, 66%).

Methyl 2-azido-4-O-benzyl-6-O-(4-chlorobenzyl)-2-deoxy-3-O-pentamethylbenzyl-1-thio-β-D-glucopyranoside (36)

A suspension of sodium hydride (40 mg, 1.0 mmol, 60%) in dry DMF (5 mL) was cooled to 0° C., and a solution of methyl 2-azido-4-O-benzyl-6-O-(4-chlorobenzyl)-2-deoxy-1-thio-β-D glucopyranoside (35) (280 mg, 0.67 mmol) in dry DMF (5 mL) was added dropwise in 30 minutes. The resulting solution was stirred at room temperature for 30 minutes and pentamethylbenzyl chloride (200 mg, 1.0 mmol) was added dropwise at 0° C. The reaction mixture was stirred at room temperature for 4 hours, cooled to 0° C. and dry methanol (1 mL) was added dropwise. The reaction mixture was concentrated under reduced pressure then xylene (10 mL) was co-evaporated from the residue. The residue was in EtOAc (100 mL), washed with brine (2×100 mL), dried over $MgSO_4$ and evaporated. The resulting solid was suspended in hexane (50 mL) and filtered to give methyl 2-azido-4-O-benzyl-6-O-(4-chlorobenzyl)-2-deoxy-3-O-pentamethylbenzyl-1-thio-β-D-glucopyranoside (36) (290 mg, 76%).

2-[(1,3-dimethyl-2,4,6(1H,3H,5H)-trioxopyrimidin-5-ylidene)methylamino]-ethyl 2-azido-4-O-benzyl-6-O-(4-chlorobenzyl)-2-deoxy-3-O-pentamethylbenzyl-α,β-D-glucopyranoside (37)

A mixture of methyl 2-azido-4-O-benzyl-6-O-(4-chlorobenzyl)-2-deoxy-3-O-pentamethylbenzyl-1-thio-β-D glucopyranoside (36) (220 mg, 0.36 mmol), 2-[(1,3-dimethyl-2,4,6(1H,3H,5H)-trioxopyrimidin-5-ylidene)methylamino]-ethanol (150 mg, 0.66 mmol), molecular sieves 4A (1 g) and DMTST (138 mg, 0.66 mmol) in 1,2-dichloroethane (10 mL) was stirred at room temperature for 30 minutes. The reaction mixture was neutralized with TEA (0.5 mL) and evaporated. The residue was purified by chromatography using $CHCl_3$—MeOH 40 mL:20 drops as the mobile phase to give 2-[(1,3-dimethyl-2,4,6(1H,3H,5H)-trioxopyrimidin-5-ylidene)methylamino]-ethyl 2-azido-4-O-benzyl-6-O-(4-chlorobenzyl)-2-deoxy-3-O-pentamethylbenzyl-β-D glucopyranoside (37) (220 mg, 77%).

2-[(1,3-dimethyl-2,4,6(1H,3H,5H)-trioxopyrimidin-5-ylidene)methylamino]-ethyl 2-amino-4-O-benzyl-6-O-(4-chlorobenzyl)-2-deoxy-3-O-pentamethylbenzyl-α,β-D-glucopyranoside (38)

A mixture of 2-[(1,3-dimethyl-2,4,6(1H,3H,5H)-trioxopyrimidin-5-ylidene)methylamino]-ethyl 2-azido-4-O-benzyl-6-O-(4-chlorobenzyl)-2-deoxy-3-O-pentamethylbenzyl-β-D glucopyranoside (37) (160 mg, 0.2 mmol) and TEA (3 drops) in 1,3-propanedithiol (1 mL) was stirred at room temperature overnight. The reaction mixture was chromatographed using EtOAc—hexane 1:1 then EtOAc—MeOH 10:1 solvent systems as mobile phases to give 2-[(1,3-dimethyl-2,4,6(1H,3H,5H)-trioxopyrimidin-5-ylidene)methylamino]-ethyl 2-amino-4-O-benzyl-6-O-(4-chlorobenzyl)-2-deoxy-3-O-pentamethylbenzyl-α,β-D glucopyranoside (38) (123 mg, 80%)

2-[(1,3-dimethyl-2,4,6(1H,3H,5H)-trioxopyrimidin-5-ylidene)methylamino]-ethyl 2-[(1,3-dimethyl-2,4,6(1H,3H,5H)-trioxopyrimidin-5-ylidene)methylamino]-4-O-benzyl-6-O-(4-chlorobenzyl)-2-deoxy-3-O-pentamethylbenzyl-α,β-D glucopyranoside (39)

A mixture of 2-[1,3-dimethyl-2,4,6(1H,3H,5H)-trioxopyrimidin-5-ylidene)methylamino]-ethyl 2-amino-4-O-benzyl-6-O-(4-chlorobenzyl)-2-deoxy-3-O-pentamethylbenzyl-β-D glucopyranoside (38) (50 mg, 0.066 mmol), 1,3-dimethyl-5-[(dimethylamino)methylene]2,4,6 (1H,3H,5H)-trioxopyrimidine (Wow-reagent) (50 mg, 0.24 mmol). TEA (0.2 mL) in CHCl$_3$—MeOH 3:1 (4 mL) was stirred at room temperature for 3 hours. The reaction mixture was evaporated, the resulting residue was chromatographed using EtOAc as the mobile phase to give 2-[(1,3-dimethyl-2,4,6(1H,3H,5H)-trioxopyrimidin-5-ylidene)methylamino]-ethyl 2-[(1,3-dimethyl-2,4,6(1H,3H,5H)-trioxopyrimidin-5-ylidene) methylamino]-4-O-benzyl-6-O-(4-chlorobenzyl)-2-deoxy-3-O-pentamethylbenzyl-α,β-D glucopyranoside (39) (4 mg, 75%).

EXAMPLE 8

Selective Deprotection Study Using the Orthogonally Protected Thioglycoside Building Block, Methyl 2-azido-6-O-tert-butyldiphenylsilyl-4-O-biphenylcarbonyl-2-deoxy-3-O-(4-methoxybenzyl)-1-thio-β-D Glucopyranoside (11)

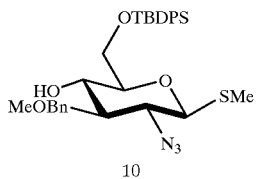
10

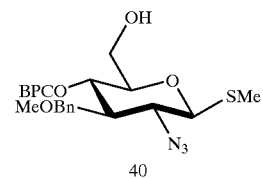
40

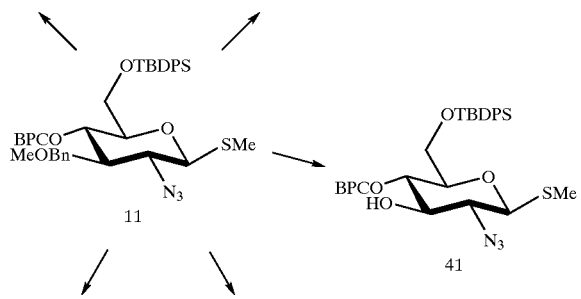
11    41

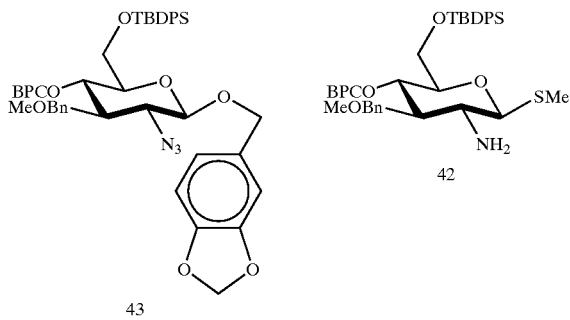
43    42

Methyl 2-azido-6-O-tert-butyldiphenylsilyl-2-deoxy-3-O-(4-methoxybenzyl)-1-thio-β-D glucopyranoside (10)

Sodium (89 mg) was reacted in dry MeOH (50 mL) then a solution of methyl 2-azido-4-O-biphenylcarbonyl-6-O-tert-butyldiphenylsilyl-2-deoxy-3-O-(4-methoxybenzyl)-1-thio-β-D glucopyranoside (11) (3 g, 3.88 mmol) in THF (25 mL) was added. The reaction mixture was stirred at 40° C. for 30 minutes, then cooled to room temperature. The solution was neutralized by Amberlite IR 120 (H$^+$) ion exchange resin. The suspension was filtered, the filtrate was evaporated. The residue was purified by chromatography using EtOAc—hexane 1:4 as the mobile phase to give methyl 2-azido-6-O-tert-butyldiphenylsilyl-2-deoxy-3-O-(4-methoxybenzyl)-1-thio-β-D glucopyranoside (10) (2.1 g, 91%).

Methyl 2-azido-4-O-biphenylcarbonyl-2-deoxy-3-O-(4-methoxybenzyl)-1-thio-β-D-glucopyranoside (40)

To a mixture of methyl 2-azido-4-O-biphenylcarbonyl-6-O-tert-butyldiphenylsilyl-2-deoxy-3-O-(4-methoxybenzyl)-1-thio-β-D-glucopyranoside (11) (150 mg, 0.19 mmol) and anhydrous AcOH (2.8 mL) in dry THF (17 mL) hydrogenfluoride-pyridine complex (2 mL) was added in a polypropylene container. The reaction mixture was kept at room temperature overnight, then diluted with EtOAC (100 mL). The resulting solution was washed with saturated sodiumhydrogen carbonate (4×100 mL), saturated brine solution (100 mL), dried over MgSO$_4$ and evaporated to dryness. The residue was purified by chromatography using EtOAC—hexane 2:5 as the mobile phase to give methyl 2-azido-4-O-biphenylcarbonyl-2-deoxy-3-O-(4-methoxybenzyl)-1-thio-β-D-glucopyranoside (40) (96 mg, 93%).

Methyl 2-azido-4-O-biphenylcarbonyl-6-O-tert-butyldiphenylsilyl-2-deoxy-1-thio-β-D-glucopyranoside (41)

A mixture of methyl 2-azido-4-O-biphenylcarbonyl-6-O-tert-butyldiphenylsilyl-2-deoxy-3-O-(4-methoxybenzyl)-1-thio-62-D-glucopyranoside (11) (150 mg, 0.19 mmol) and DDQ (52 mg, 0.23 mmol) in CH$_2$Cl$_2$—H$_2$O 9:1 (5 mL) was stirred at room temperature for 3 hours. The reaction mixture was washed with saturated NaHCO$_3$ solution (3×3 ml), dried over MgSO$_4$ and evaporated. The residue was purified by chromatography using EtOAc—hexane 15:85 as the mobile phase to give methyl 2-azido-4-O-biphenylcarbonyl-6-O-tert-butyldiphenylsilyl-2-deoxy-1-thio-β-D-glucopyranoside (41) (116 mg, 92%).

Methyl 2-amino-4-O-biphenylcarbonyl-6-O-tert-butyldiphenylsilyl-2-deoxy-3-O-(4-methoxybenzyl)-1-thio-62-D-glucopyranoside (42)

A mixture of methyl 2-azido-4-O-biphenylcarbonyl-6-O-tert-butyldiphenylsilyl-2-deoxy-3-O-(4-methoxybenzyl)-1-thio-β-D-glucopyranoside (11) (150 mg, 0.19 mmol) and TEA (3 drops) in 1,3-propanedithiol (1 mL) was stirred at room temperature overnight. The reaction mixture was chromatographed using EtOAc—hexane 15:85 then EtOAc—hexane 1:1 solvent systems as mobile phases to give methyl 2-amino-4-O-biphenylcarbonyl-6-O-tert-butyldiphenylsilyl-2-deoxy-3-O-(4-methoxybenzyl)-1-thio-β-D-glucopyranoside (42) (130 mg, 91%).

3,4-Methylenedioxybenzyl 2-azido-4-O-biphenylcarbonyl-6-O-tert-butyldiphenylsilyl-2-deoxy-3-O-(4-methoxybenzyl)-α,β-D-glucopyranoside (43)

A mixture of methyl 2-azido-4-O-biphenylcarbonyl-6-O-tert-butyldiphenylsilyl-2-deoxy-3-O-(4-methoxybenzyl)-1-thio-β-D-glucopyranoside (11) (200 mg, 0.26 mmol), 3,4-methylenedioxybenzyl alcohol 59 mg, 0.39 mmol), molecular sieves 4A (1 g) and methyltriflate (106 mg, 0.65 mmol) in 1,2-dichloroethane (10 mL) was stirred at room temperature overnight. The reaction mixture was neutralized with TEA (0.5 mL) and evaporated. The residue was purified by chromatography using EtOAc—hexane 15:85 as the mobile phase to give 3,4-methylenedioxybenzyl 2-azido-4-O-biphenylcarbonyl-6-O-tert-butyldiphenylsilyl-2-deoxy-3-O-(4-methoxybenzyl)-α,β-D-glucopyranoside (43) (173 mg, 76%).

It will be apparent to the person skilled in the art that while the invention has been described in some detail for the purpose of clarity and understanding. various modifications and alterations to the embodiments and methods described herein may be made without departing from the scope of the invention concept disclosed in this specification.

References cited herein are listed below, and are incorporated herein by this reference.

REFERENCES

Merrifield, R. B. Pept., Proc. Am. Pept. Symp., 5$^{th}$, 1977 488.

Wong, C-H, Ye, X-S and Zhang, Z. J. Am. Chem. Soc., 1998 120 7137–7138.

Wunberg, T. Kallus, C., Opatz, T., Henke, S., Schmidt, W., and Kunz, H. Angew. Chem. Intr. Ed., 1988 37 2503–2505.

What is claimed is:

1. An orthogonally protected monosaccharide building block of Formula I or Formula II

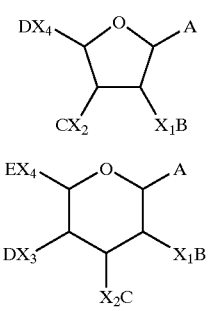

in which

A is a leaving group selected from the group consisting of halogen, trichloroacetimidoyl, sulphoxide, —O-alkenyl; and —SR, where R is alkyl, alkenyl, alkynyl, cycloalkyl or aryl.

$X_1$, $X_2$, and $X_3$ are independently selected from H, O, N, or $N_3$, with the proviso that only one of $X_1$, $X_2$, and $X_3$ is H, N or $N_3$ in any molecule;

$X_4$ is —CH$_2$O; and

B, C, D and E are different and of them B, C, or D is absent if the corresponding $X_1$ to $X_3$ is H or $N_3$, and B, C, D and/or E are selected from protecting groups which can be cleaved orthogonally in any order, such that the cleavage conditions do not compromise the stability of the other protecting or functional groups on the monosaccharide building block, wherein the protecting groups for hydroxy protection are selected from the group consisting of acyl-type protecting groups, carbonates, t-butyldiphenylsilyl, triisopropylsilyl, trimethylsilylethyl, triphenylsilylethyl, trifluoromethyl, trichloromethyloxymethyl, trichloromethyfoxycarbonate, ethoxyethyl, cyanoethyl, NSC (p-ntirobenzyl-sulphonylethyloxycarbonyl), p-nitrobenzyl-sulphonylethyl, naphthylmethyl, substituted naphthylmethyl, p-methoxybenzyl, 3,4-dimethoxybenzyl, 2,4,6-trimethoxybenzyl, 3,4-methylenedioxybenzyl, acylamidobenzyl, azidobenzyl, p-azido-m-chlorobenzyl, allylic protecting groups, o-nitrobenzyloxycarbonate, o-nitrobenzyl, dinitrobenzyl, 2-oxo-1,2-diphenylethyl, methylthioethyl, acyloxybenzyl and benzylthioethyl; and for amino protection are selected from the group consisting of Dde (N-[1-(4,4-dimethyl-2,6-dioxocyclohex-1-ylidene)ethyl]), Wow ((1,3-dimethyl-2,4,6-(1H,3H,5H)-trioxopyrimidin-5-ylidene) methyl), tetraphthaloyl, dichlorophthaloyl, 2,5-dimethyl-pyrrol benzyloxycarbonyl, and pentenyl.

2. A monosaccharide building block according to claim 1, which is a compound of Formula III

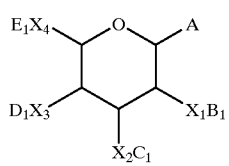

III in which:

A, $X_1$, $X_2$, $X_3$ and $X_4$ are as defined for Formulae I and II; and $B_1$, $C_1$, $D_1$ and $E_1$ are orthogonal carbohydrate protecting groups which for hydroxy protection are selected from the group consisting of acyl-type protecting groups, carbonates, t-butyldiphenylsilyl, triisopropylsilyl, trimethylsilylethyl, triphenylsilylethyl, p-methoxybenzyl, 3,4-dimethoxybenzyl, 2,4,6-trimethoxybenzyl, 3,4-methylenedioxybenzyl, acylamidobenzyl, azidobenzyl, p-azido-m-chlorobenzyl, o-nitrobenzyloxycarbonate, o-nitrobenzyl, dinitrobenzyl and 2-oxo-1,2-diphenylethyl; and for amino protection are selected from the group consisting of Dde, Wow, tetraphthaloyl, dichlorophthaloyl, 2,5-dimethyl-pyrrol, benzyloxycarbonyl, and pentenyl.

3. A monosaccharide building block according to claim 1, which is a compound of Formula IV

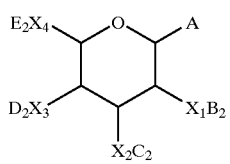

IV in which

A, $X_1$, $X_2$, $X_3$ and $X_4$ are as defined for Formulae I and II; and $B_2$, $C_2$, $D_2$ and $E_2$ are orthogonal carbohydrate protecting groups which for hydroxy protection are selected from the group consisting of acyl-type protecting groups and carbonates, and for amino protection are selected from the group consisting of Dde, Wow, tetraphthaloyl, dichlorophthaloyl, 2,5-dimethyl-pyrrol, benzyloxycarbonyl, and pentenyl.

4. A monosaccharide building block according to claim 3, in which the protecting groups are selected from the group consisting of levanoyl, chloroacetate, p-methoxybenzyloxycarbonyl and 2-trimethylsilylethylcarbonate.

5. A monosaccharide building block according to claim 1, which is a compound of Formula V

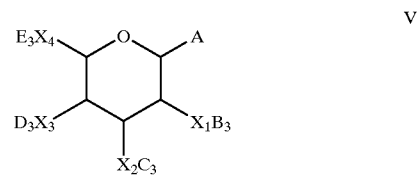

V in which

A, $X_1$, $X_2$, $X_3$ and $X_4$ are as defined for Formulae I and II; and $B_3$, $C_3$, $D_3$ and $E_3$ are orthogonal carbohydrate protecting groups at least one of which is selected from the group consisting of acyl-type protecting groups, carbonates, Dde, Wow, tetraphthaloyl, dichlorophthaloyl, 2,5-dimethyl-pyrrol, benzyloxycarbonyl, and pentenyl; and the remainder being selected from the group consisting of t-butyldiphenylsilyl, triisopropylsilyl, trimethylsilylethyl, triphenylsilylethyl, trifluoromethyl, trichloromethyloxymethyl, trichloromethyloxycarbonate, ethoxyethyl, cyanoethyl, NSC (p-nitrobenzyl-sulphonylethyloxycarbonyl), p-nitrobenzyl-sulphonylethyl, naphthylmethyl, substituted naphthylmethyl, p-methoxybenzyl, 3,4-dimethoxybenzyl, 2,4,6-trimethoxybenzyl, 3,4-methylenedioxybenzyl, acylamidobenzyl, azidobenzyl, p-azido-m-chlorobenzyl, allylic protecting groups, o-nitrobenzyloxycarbonate, o-nitrobenzyl, dinitrobenzyl, 2-oxo-1,2-diphenylethyl, methylthioethyl, acyloxybenzyl and benzylthioethyl.

6. A method of synthesis of a molecule selected from the group consisting of glycoconjugates of non-carbohydrate molecules, neo-glycoconjugates and oligosaccharides, comprising the step of glycosylating the molecule with a monosaccharide building block according to claim 1.

7. A method according to claim 6, in which the molecule comprises one or more compounds in which substituents are linked to a pyranose or furanose ring.

8. A method according to claim 6, in which the synthesis is carried out in solution.

9. A method according to claim 6, in which the synthesis is carried out on a solid-phase support.

* * * * *

UNITED STATES PATENT AND TRADEMARK OFFICE
CERTIFICATE OF CORRECTION

PATENT NO. : 6,953,850 B1
DATED : October 11, 2005
INVENTOR(S) : Gyula Dekany, John Papagerogiou and Laurent Francois Bornaghi It is certified that error appears in the above-identified patent and that said Letters Patent is hereby corrected as shown below:

Column 1,
Line 66, change "levulinyl" to -- levulinoyl --.

Column 3,
Line 47, change "levanoyl" to -- levulinoyl --.

Column 4,
Line 65, change "levanoyl" to -- levulinoyl --.

Column 32,
Line 11, change "levanoyl" to -- levulinoyl --.

Signed and Sealed this

Twenty-ninth Day of November, 2005

JON W. DUDAS
*Director of the United States Patent and Trademark Office*